(12) United States Patent
Rau et al.

(10) Patent No.: US 12,053,285 B2
(45) Date of Patent: *Aug. 6, 2024

(54) REAL TIME BIOMETRIC RECORDING, INFORMATION ANALYTICS, AND MONITORING SYSTEMS AND METHODS

(71) Applicant: Sackett Solutions & Innovations, LLC, Carmel, IN (US)

(72) Inventors: Hans Rau, Carmel, IN (US); Nemoy Rau, Carmel, IN (US); Visveshwar Baskaran, Carmel, IN (US); Ramarao Inguva, Huntsville, AL (US)

(73) Assignee: Sackett Solutions & Innovations, LLC, Carmel, IN (US)

( * ) Notice: Subject to any disclaimer, the term of this patent is extended or adjusted under 35 U.S.C. 154(b) by 709 days.

This patent is subject to a terminal disclaimer.

(21) Appl. No.: 17/130,753

(22) Filed: Dec. 22, 2020

(65) Prior Publication Data

US 2021/0106265 A1    Apr. 15, 2021

Related U.S. Application Data

(62) Division of application No. 14/807,162, filed on Jul. 23, 2015, now Pat. No. 10,874,340.

(Continued)

(51) Int. Cl.
| | | |
|---|---|---|
| *A61B 5/00* | (2006.01) | |
| *A61B 5/16* | (2006.01) | |
| *A61B 3/113* | (2006.01) | |
| *A61B 5/0205* | (2006.01) | |
| *A61B 5/021* | (2006.01) | |
| *A61B 5/024* | (2006.01) | |
| *A61B 5/0533* | (2021.01) | |
| *A61B 5/08* | (2006.01) | |
| *A61B 5/11* | (2006.01) | |
| *A61B 5/145* | (2006.01) | |
| *A61B 5/318* | (2021.01) | |
| *A61B 5/369* | (2021.01) | |

(52) U.S. Cl.
CPC ............ *A61B 5/165* (2013.01); *A61B 5/4884* (2013.01); *A61B 3/113* (2013.01); *A61B 5/0205* (2013.01); *A61B 5/021* (2013.01); *A61B 5/024* (2013.01); *A61B 5/0533* (2013.01); *A61B 5/0816* (2013.01); *A61B 5/1116* (2013.01); *A61B 5/14542* (2013.01); *A61B 5/318* (2021.01); *A61B 5/369* (2021.01); *A61B 5/442* (2013.01); *A61B 5/4803* (2013.01)

(58) Field of Classification Search
CPC .............................. A61B 5/165; A61B 5/4884
See application file for complete search history.

(56) References Cited

U.S. PATENT DOCUMENTS 9,357,921 B2 *  6/2016  Chang .................... G16H 50/30
9,521,973 B1 * 12/2016  Beiski .................... A61B 5/168
(Continued)

*Primary Examiner* — John R Downey
(74) *Attorney, Agent, or Firm* — Hartman Global IP Law; Gary M. Hartman; Domenica N. S. Hartman

(57) ABSTRACT

The present invention provides a novel system of hardware designed to capture and process in real time clinical observations of patient responses and reactions in different clinical and patient settings and situations, comprising: a patient biometric data recording system in a clinical office, a mobile real time episode or event data recording device system or a wearable device recording system.

33 Claims, 9 Drawing Sheets

Related U.S. Application Data

(60) Provisional application No. 62/028,369, filed on Jul. 24, 2014.

(56) References Cited

U.S. PATENT DOCUMENTS

| | | | |
|---|---|---|---|
| 9,685,174 B2* | 6/2017 | Karam | A61B 5/6898 |
| 2006/0052720 A1* | 3/2006 | Ross | A61B 5/00 |
| | | | 600/595 |
| 2007/0066874 A1* | 3/2007 | Cook | A61B 5/0533 |
| | | | 128/903 |
| 2009/0093688 A1* | 4/2009 | Mathur | H04N 7/18 |
| | | | 600/300 |
| 2010/0010371 A1* | 1/2010 | Zayfert | G16H 20/70 |
| | | | 600/558 |
| 2014/0121540 A1* | 5/2014 | Raskin | G16H 40/63 |
| | | | 600/479 |
| 2016/0022193 A1* | 1/2016 | Rau | A61B 5/4884 |
| | | | 600/595 |

* cited by examiner

REAL TIME BIOMETRIC RECORDING, INFORMATION ANALYTICS, AND MONITORING SYSTEMS AND METHODS

CROSS-REFERENCE TO RELATED APPLICATIONS

This U.S. non-provisional patent application is a division patent application of co-pending U.S. patent application Ser. No. 14/807,162, filed Jul. 23, 2015, which claims the benefit of and/or priority to U.S. provisional patent application Ser. No. 62/028,369, filed Jul. 24, 2014. The contents of these prior applications are incorporated herein by reference.

FIELD OF THE INVENTION

The present invention relates to systems and methods adopted for health monitoring of individuals. More specifically, the invention relates to systems and methods to measure behavioral health changes in individuals in different settings. The invention further provides for processing of acquired data by applying statistical, mathematical, and analytical tools to infer changes in the patient's mental health.

BACKGROUND

Treatment and monitoring of mental health patients, more specifically those with mental health illnesses like panic attacks, anxiety and depression, have a limited set of objective clinical measurement tools available compared to general health practices. Use of biometric measurement tools as measurement and monitoring devices is disclosed in several patents and patent applications. U.S. Pat. No. 7,540,841 describes a system that collects data on an individual's daily activities to infer their mental health. U.S. Pat. No. 7,894,849 describes a method of collecting data through multiple sensors. WO2012108935 describes a health management system using a mobile communication device to communicate biometric sensor data through a server. US 20130009993, US 20130011819, US 20130012790, and US 201300113331 disclose methodology to provide real-time feedback of health information for an employee from a set of health sensors, while the employee is engaged in work duties. US20130281798 discloses methods and systems to periodically monitor the emotional state of a subject, comprising the steps of: exposing the subject to a plurality of stimuli during a session; acquiring objective data from a plurality of monitoring sensors, wherein at least one sensor measures a physiological parameter; transferring the data to a database; and processing the data to extract objective information about the emotional state of the subject. There is still a long felt and unmet need for improved methods and apparatus for treatment and monitoring of mental health patients.

SUMMARY OF THE INVENTION

The present invention provides new systems and methods for real-time measurement of objective, autonomic physiological parameters that allow for monitoring of mental health illnesses and emotional health changes in ways not previously contemplated. More specifically, the invention provides methods and multiple sensor(s) integrated devices for gathering real-time, autonomic physiological parametric data from a patient in different settings (e.g., in a patient's clinical examination; administering of standardized mental health tests or measurements to a patient; and when a patient is experiencing an anxiety episode or panic attack).

While not intended to be limiting, the following are some of the objects of the invention:

To Link types and degrees of intensity of stimuli to nervous system reactions through biometric sensor data and verbal responses through language, cognitive and speech communication analytics;

To improve inferential discrimination among different types and severity of mental illnesses through objective measurements and longitudinal information of higher specificity and accuracy;

To improve diagnosis, prognosis, treatments' efficacies and patient monitoring;

To capture objective measurements of a dynamic stress event through event monitoring device systems and develop a comprehensive patient illness condition;

To provide patient feedback and visualization of objective comparisons of illness progress between successive visits;

To provide wearable multi-sensor integrated devices with data fusion analytics designed to monitor and record patients' vital parameters, sleep patterns and patient reported changes in their daily life patterns over a specific time period;

To create and provide real time evidence-based measurable and objective inter- and intra-patient longitudinal information to the physicians in mental healthcare for the first time. This facilitates the primary care physicians and specialists to employ protocols and patient treatment practices for mental health similar to other medical fields and physical illnesses;

To provide treatment and patient progress assessment through objective measurements for mental illnesses.

In a first aspect, the present invention provides apparatus (multiple sensors integrated devices) for real-time acquisition and analysis of a set of objective biometric data during a patient examination or as a patient experiences a mental disorder episode or event.

In a first embodiment, the apparatus comprises: at least two integrated audio-visual cameras to record speech and tone (fluctuations and perturbations), verbal response linguistic content, facial features, and pupil size.

In a preferred embodiment, the device has the capability to communicate by Bluetooth or Wifi.

In a third embodiment, the mental disorder is selected from but not limited to: anxiety; post-traumatic stress disorder (PTSD); depression; attention deficit disorder; comorbidity with another physical or mental illness; addiction withdrawal; and psychiatric presentation, reaction, or complication from a medical treatment or surgery.

In a preferred embodiment, the mental disorder is anxiety or depress n.

In a more preferred embodiment, the mental disorder is anxiety.

In a fourth embodiment, the apparatus comprises: a processor and associated software for applying data analytics on the response data elements to provide trend analysis.

In a preferred embodiment, the software applies techniques from hierarchical linear models, nonlinear mixed models, and/or generalized mixed models on the data elements for data analytics.

In another preferred embodiment, the software applies traditional aggregation and cluster differentiation statistical techniques to present the data to healthcare decision makers with graphical and intuitive comparisons.

In another preferred embodiment, the software applies a mathematical algorithm incorporating sequential filtration of noise, expected deviations and correlated information of Autonomic Physiological Parameters (referred as APPs hereafter) and changes while testing and applying statistical tools and techniques to generate the information outputs in graphical and comparative data formats.

In a sixth embodiment, the apparatus comprises: a reference database that performs a series of real-time analyses and computations, graphics-based applications, and data storage.

In a preferred embodiment, the database is connected to various remote-testing locations and stores all the data, statistical tools, and programs.

In another preferred embodiment, an individual's records are stored in this database, such as those relating to the initiation of each query and an updated subject's history.

In another embodiment, these records can be sent to the decision makers in real-time.

In a second aspect, the invention provides a system of hardware designed to capture and process in real time clinical observations of patient responses and reactions in different clinical and patient settings and situations, comprising: a patient biometric data recording system in a clinical office, a mobile real time episode or event data recording device system, or a wearable device recording system.

In a first embodiment, the system of hardware comprises: a patient biometric data recording system in a clinical office.

In a second embodiment, the system of hardware comprises: a mobile real time episode or event data recording device system.

In a third embodiment, the system of hardware comprises: a wearable device recording system.

In a fourth embodiment, the system of hardware comprises: one or more biometric sensors integrated into devices with user option to select one or more of the sensors, and devices with a capability to process, analyze and fuse sensors' raw output data through software programs and analytical tools.

In a fifth embodiment, the sensors' raw output data is transmitted to a cloud-based server architecture for processing, analysis and integration into an information database.

In a sixth embodiment, the data recording system comprises: one or more sensors designed to capture and measure changes in physiological parameters selected from the group consisting of: blood pressure, pulse rate, respiratory rate, breathing rate, blood oxygenation level, galvanic skin conductance, facial skin tone, changes in pupil size, tracking pupil movements, changes and frequency of eyelid flutter, changes in sitting postures or bodily movements, unusual gestures or motions, movement of the leg or hand muscles, changes in voice pitch and tone and perturbation and speech rate, changes in facial muscles, brain electrical activity, and heart electrical activity.

In a seventh embodiment, the mobile real time episode or event data recording device system or wearable device recording system are used for monitoring patients customized for different illnesses in their daily activities and optionally activating customized pre-recorded therapy sessions between office examinations.

In an eighth embodiment, the different clinical and patient settings and situations are selected from the group consisting of: periodic or emergency clinical physical and mental health examinations, psychometric testing and measurement sessions, recording and monitoring patient physiological parameters in daily activities, and during an episode of anxiety, stress, or panic attack.

In a third aspect, the invention provides a method of acquiring objective data relating to biometric parameters of an individual to diagnose, devise a treatment plan, or monitor emotional and mental state of an individual, comprising one of more of the following steps:
 a. creating baseline biometric parameters of the individual;
 b. generating and obtaining the initial set of objective biometric data that quantify biometric and physiological parameters and speech content and verbal communication responses to stimuli;
 c. producing an individual record containing objective data;
 d. repeating the generating and obtaining objective biometric data process to quantify biometric and physiological parameters and speech content and verbal communication responses to stimuli to create the subsequent sets of biometric data;
 e. transferring the data to a database;
 f. quantitatively comparing the initial, subsequent and successive sets of objective records to detect changes in mental health condition of the individual; and
 g. generating patient illness condition and information by integrating the biometric data changes and inferences from patient examination and of any other relevant illnesses and conditions.

It will be appreciated that all combinations and orders of the steps recited above are contemplated as further embodiments of the invention, several examples of which are recited below in embodiments 1-4:

In a first embodiment, the method comprises the step of:
 a. generating patient illness condition and information by integrating the biometric data changes and inferences from patient examination and of any other relevant illnesses and conditions.

In a second embodiment, the method comprising steps of:
 a. generating and obtaining the initial set of objective biometric data that quantify biometric and physiological parameters and speech content and verbal communication responses to stimuli;
 b. producing an individual record containing objective data;
 c. and transferring the data to a database.

In a third embodiment, the method comprises the steps of:
 a. quantitatively comparing the initial, subsequent and successive sets of objective records to detect changes in mental health condition of the individual; and
 b. generating patient illness condition and information by integrating the biometric data changes and inferences from patient examination and of any other relevant illnesses and conditions.

In a fourth embodiment, the method comprises the following steps:
 a. creating baseline biometric parameters of the individual;
 b. generating and obtaining the initial set of objective biometric data that quantify biometric and physiological parameters and speech content and verbal communication responses to stimuli;
 c. producing an individual record containing objective data;
 d. repeating the generating and obtaining objective biometric data process to quantify biometric and physiological parameters and speech content and verbal communication responses to stimuli to create the subsequent sets of biometric data;

e. transferring the data to a database;

f. quantitatively comparing the initial, subsequent and successive sets of objective records to detect changes in mental health condition of the individual; and g. generating patient illness condition and information by integrating the biometric data changes and inferences from patient examination and of any other relevant illnesses and conditions.

In a fifth embodiment, the stimuli are components of a mental state examination.

In a sixth embodiment, the stimuli are presented through visual, oral, aural, kinesthetic or written methods.

In a seventh embodiment, the stimuli are comprised of structured or standardized stimuli.

In an eighth embodiment, the standardized stimuli are selected from a database of questions, mental and physical activities, or psychometric and aptitude tests.

In a ninth embodiment, the biometric and physiological parameters are selected from the group consisting of: blood pressure, pulse rate, respiratory rate, breathing rate, blood oxygenation level, galvanic skin conductance, facial skin tone, changes in pupil size, tracking pupil movements, changes and frequency of eyelid flutter, changes in sitting postures or bodily movements, unusual gestures or motions, movement of the leg or hand muscles, changes in voice pitch and tone and perturbation and speech rate, changes in facial muscles, brain electrical activity, and heart electrical activity.

In a tenth embodiment, the language and verbal response analytics indicate significant changes, if any, of the patient's coping mechanisms to manage pressures, stresses and self-control.

In an eleventh embodiment, the quantitative comparison of changes is the change between the initial, subsequent, and successive sets of biometric data by the change in terms of at least one of frequency, duration, intensity, deviations, and summary statistics of the objective data to improve specificity for clinician diagnosis and to categorize into low, medium, or high severity levels for each illness type diagnosed by the clinician.

In a twelfth embodiment, the initial and subsequent sets of biometric parameters comprise a measure of at least one of somatic and autonomic nervous system reactions of the individual.

In a thirteenth embodiment, the method further comprises the step of: quantitatively comparing at least one of the initial and subsequent sets patient illness condition and information with other individuals diagnosed with the same mental illness to generate inter- and intra-patient longitudinal information.

In a fourteenth embodiment, the method further comprises the step of: inputting other relevant patient illnesses and conditions information selected from the group consisting of: genetic risk factors, blood tests, relevant pharmacogenomics tests, brain scans and other body imaging scans.

In a fifteenth embodiment, the method further comprises the step of: assessing resilience of the individual based on the quantitative comparing of the first and subsequent objective records.

In a sixteenth embodiment, the method further comprises the step of: assessing coping skills of the individual based on the quantitative comparing of the first and subsequent objective records.

In a seventeenth embodiment, the method further comprises the step of: assessing a dysfunctionality of the individual based on the quantitative comparing of the first and subsequent objective records.

In an eighteenth embodiment, the method further comprises the step of: assessing the patient progress of the individual based on the quantitative comparing of the first and subsequent objective records.

In a nineteenth embodiment, the method further comprises the step of: assessing the treatment efficacy of the individual based on the quantitative comparing of the first and subsequent objective records.

In a fourth aspect, the present invention provides a method of capturing and processing clinical observations of patient responses and reactions in real-time in different settings.

In a first embodiment, the different settings include: periodic or emergency mental health examinations, psychometric testing and measurement sessions, and during an episode of anxiety, stress or panic attack.

In a fifth aspect, the present invention provides a method of periodically monitoring in real-time the mental state of a subject experiencing a mental health disorder episode, comprising one or more of the following steps:

a. acquiring objective, real-time, audio-visual data on a mobile device during the episode related to facial features, pupil size changes, and voice patterns;

b. transferring the data to a database;

c. processing the data to extract objective information about the mental state of the subject;

d. generating a clinician-customized offsite interview or therapy session; and e. downloading the session to the mobile device.

It will be appreciated that all combinations and orders of the steps recited above are contemplated as further embodiments of the invention, several examples of which are recited below in embodiments 1-3.

In a first embodiment, the present invention provides a method of periodically monitoring in real-time the mental state of a subject experiencing a mental health disorder episode, comprising the steps of:

a. acquiring objective, real-time, audio-visual data on a mobile device during the episode related to facial features, pupil size changes, and voice patterns; and transferring the data to a database.

In a 2nd embodiment, the present invention provides a method of periodically monitoring in real-time the mental state of a subject experiencing a mental health disorder episode, comprising the steps of:

processing the data to extract objective information about the mental state of the subject;

generating a clinician-customized offsite interview or therapy session; and downloading the session to the mobile device.

In a third embodiment, the present invention provides a method of periodically monitoring in real-time the mental state of a subject experiencing a mental health disorder episode, comprising the steps of:

a. acquiring objective, real-time, audio-visual data on a mobile device during the episode related to facial features, pupil size changes, and voice patterns;

b. transferring the data to a database;

c. processing the data to extract objective information about the mental state of the subject;

d. generating a clinician-customized offsite interview or therapy session; and e. downloading the session to the mobile device.

In a fourth embodiment, the method further comprises the step of: monitoring a vital physiological parameter selected from blood pressure, pulse rate, skin conductively, breathing rate, and temperature.

In a fifth embodiment, the mental health disorder is selected from: anxiety, post-traumatic stress disorder; depression; attention deficit disorder; co-morbidity with another disease; addiction withdrawal; and psychiatric presentation, reaction, or complication from a medical treatment or surgery.

In a sixth embodiment, the mental health disorder is anxiety, depression or panic attack.

In a seventh embodiment, the mental health disorder is anxiety.

In an eighth embodiment, the processing of data comprises: comparing the acquired data in the current session with corresponding data from a previous recorded session and computing the deviations thereof.

In a ninth embodiment, the processing of data includes tracking the totality of mental state, the dependent risk classifications, and their changes from session to session.

In a tenth embodiment, the risk classification includes classification of the subject into low, medium, or high-risk treatment plan categories.

In an eleventh embodiment, the risk classification includes the classification of the stress severity level of the subject.

In a twelfth embodiment, the processing of data comprises linking and integrating additional background information derived from the subject's mental health, physical health, sleep records, or addiction history to infer changes in mental state.

In a thirteenth embodiment, the objective information comprises an assessment of the subject's mental state progression in response to prescribed treatment plans.

It is understood that all allowable combinations (i.e., two or more) of the embodiments described above (and elsewhere herein) are contemplated as further embodiments of the invention.

BRIEF DESCRIPTION OF THE FIGURES

The present invention is described with reference to the accompanying Figures, which are not intended to limit the scope thereof.

DETAILED DESCRIPTION

Overview

Figure 1:
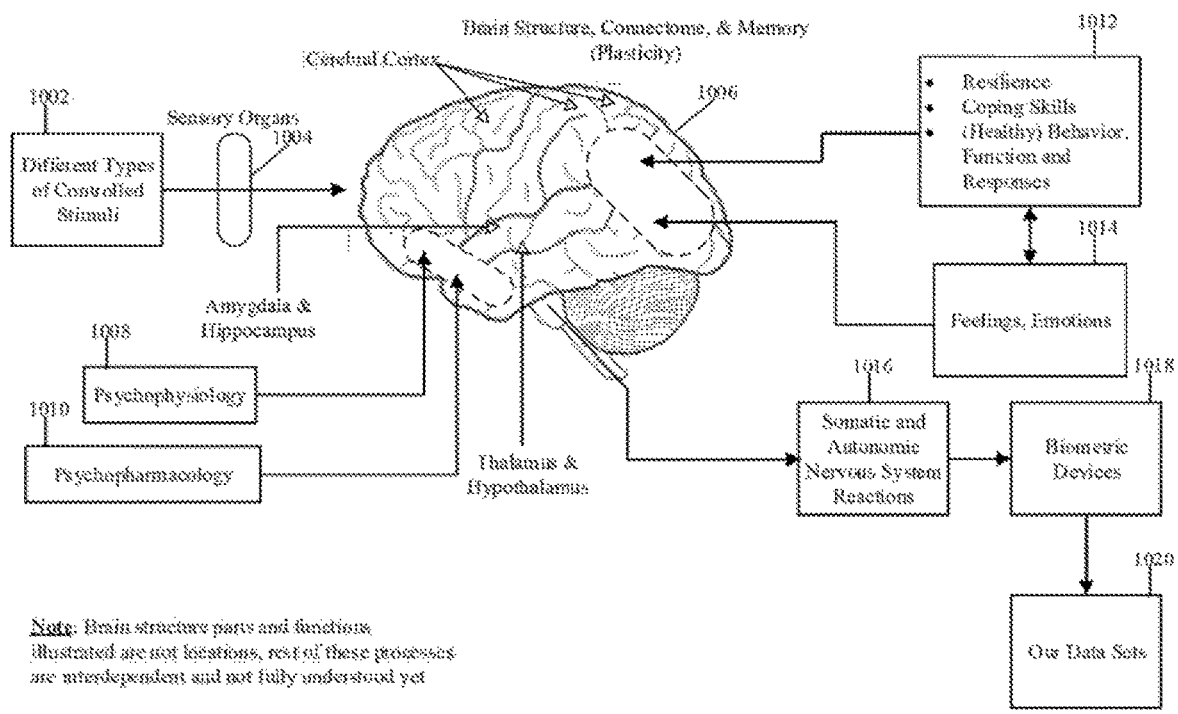
FIG. 1 is a block diagram depicting the relationship between central nervous system (CNS) stimulus and the biometric reactions.

Behavioral health (an umbrella term referring to a continuum of services for individuals at risk of, or suffering from, mental, behavioral, addictive disorders, or emotional disturbances) patient diagnosis, monitoring, and treatment practices do not yet have protocols or systems to create objective patient tests or measurements, due to at least the following factors: (1) the complexity of psychophysiology and psychopharmacology of many mental diseases and disorders; (2) many types of anxieties and depression conditions are caused by variations in individual genetics, biochemistry, environmental/social factors, individual's specific social, health and family details (e.g., age, gender, medical history, family history and dynamics), traumatic events, and addictions; (3) continuous changes in brain's neural architecture (connectome and synapses) from new knowledge, learning and many life experiences resulting in new connections (generally termed 'plasticity'); and (4) many overlapping symptoms among different mental illnesses. Currently, patient diagnosis and progress monitoring is performed by clinicians (defined hereafter that include physicians, clinical staff, psychologists and behavioral health therapists) by their observations during patient examination process and from the description of symptoms, feelings, triggers, events and behavior as self-reported by the patient. Real-time actual stress event observation by a trained clinician of a mental health episode, event, or panic attack has not been hitherto possible.

The present invention provides a richer set of somatic and autonomic nervous system reactions of the patient evoked by controlled and structured stimuli as currently employed by clinicians in their patient examination. The resulting data set is captured by an integrated system containing a plurality of biometric sensor(s) integrated devices. The quality and quantity of information obtained in this process is well beyond any human observation and analytical skills.

Specifically, the present approach provides: intra- and inter-patient comparisons through data analytics and tools; real-time episode recording and data analytics; and linking of various types of stimuli (clinician controlled during patient exam through clinical questions, referred to as Structured Stimuli hereafter, to elicit patient responses and therefrom develop a profile of patient's behavioral illness conditions and patient function; and standardized measures or tests routinely used in psychiatry practice, referred to as Standardized Stimuli hereafter, to nervous system reactions. This creates much more powerful inferential data sets, since we predominately monitor a patient's changes in speech tone (fluctuations and perturbations), and speech and language functional analysis of the patient's oral responses, the most important input in a clinician's assessment. The present invention links the types and degrees of intensity of stimuli (e.g., discriminating, eliciting, emotional, reinforcement, nominal, functional, or pseudo-reflex) to the nervous system's reactions; validates the diagnosis and patient progress via evaluation by experienced and trained clinicians; and aggregates this information for various mental illnesses thereby creating a valuable database for future evidence-based clinical practices. This new approach applies many analytical techniques and tools, such as: cluster analysis; variations within and between clusters among datasets of different time periods and episodes; and compactness or spread of significant parameters among patients of similar background and mental health condition.

Many psychiatric patients with anxieties and depressions are examined and treated by primary care physicians. In the process of developing a personalized effective treatment, often these physicians may have to employ 'trial and error' processes. This is due to low specificity and sensitivity in differential diagnosis currently possible, because of the lack of objective measurements in behavioral healthcare (unlike in other medical fields) and many overlapping symptoms presented among various types of anxieties and depressive disorders. The systems of the invention can discriminate between anxieties and certain types of depressions with a higher degree of specificity than was hitherto possible, thereby improving the clinicians' therapy and medication choices. In addition, these systems (hardware, software tools and content defined as the various types of Structured and Standardized stimuli hereafter) have the potential to provide an important breakthrough in the telepsychiatry practice.

The inventors have developed methodology to link types of stimuli to types of emotions and their intensity, as described below:

Types of Stimuli

Questions in the standard clinical tests and respective patient responses to those questions are grouped into various categories. Clinicians administering and interpreting these tests use these categories, compare with anticipated or expected responses for standardized clinical tests based on a patient's illness and combine the information of significant biometric changes and thresholds provided by this system through the real-time data analytics.

Emotions Grouping six primary emotions (anger, happiness, surprise, disgust, sadness, and fear as described by Paul Ekman) are classified, and further divided into secondary and tertiary emotions (as described in Shaver et al, 2001), if the clinician feels the need. Standardized clinical test questions are matched with the expected emotion for that question.

Intensity biometric patient response data are summarized by groupings (typically four or more types) such as voice, pitch, and tonal changes; response linguistic content; and changes in: facial expressions, eye movements, pupil width, skin conductivity, perspiration, temperature, pulse, blood pressure, blood oxygenation, and/or breathing rate. Differences from a patient's baseline (resting) information are computed, and those differences showing significance (statistical) and/or above the thresholds developed from each characteristic illness group averages are summarized into three features: duration, frequency, and intensity levels. These data elements are organized into a matrix configuration to perform inferential analytics and severity indices for different illnesses. This objective patient measurement data from the present invention helps the clinicians by providing real-time information with higher specificity. This leads to more accurate and improved diagnosis for different types of anxieties, depressions, and their severity levels, thereby improving the differential diagnosis and treatment processes.

The present invention can be used to diagnose and treat many mental health disorders and illnesses, such as, but not limited to: anxiety [e.g., generalized anxiety disorder, panic disorders, phobias, obsessive-compulsive disorders (OCD), post-traumatic stress disorder (PTSD); attention deficient disorder (ADD), and attention deficit hyperactivity disorder (ADHD)]; depressive disorder (e.g., dysthymia, depression in the elderly, postpartum depression); stress or mild depression caused by comorbidity with other health conditions (e.g., strokes, cardiac procedures, cancer treatments, major accidents, and major surgeries); and cognitive impairments related to aging. Applicants note that these are standard terms of usage, as per the Diagnostic and Statistical Manual of Mental Disorders, Fifth Edition (DSM-V), the 2013 update to the American Psychiatric Association's (APA) classification and diagnostic tool.

Specific Embodiments

Clinicians conduct Mental State Examinations (MSE) to assess a patient's mental health condition. MSE is a structured way of observing and describing a patient's current state of mind under the domains of appearance, attitude, behavior, mood and affect, speech, thought process, thought content, perception, cognition, insight and judgment (Trzepacz, P T; Baker R W (1993). The Psychiatric Mental Status Examination. Oxford, U.K.: Oxford University Press. p. 202. ISBN 0-19-506251-5). FIG. 1 illustrates this link between stimuli processed in the brain structure to the central nervous system's function, transmitted through the somatic and autonomic peripheral nervous systems. Some of these visible responses are observed and assessed in the clinical examination by trained clinicians. Individual biometric devices are the means to capture the same set of data observed by the clinicians. The system's biometric devices are programmed and integrated to capture many additional types of valuable, related data possible beyond any human observation.

For a number of mental illnesses, the primary input for diagnosis and for assessing a patient's progress is the patient's own description and recall of her episodes. If a detailed, real-time audio-video recording of a patient's anxiety episode (e.g., panic attack) is also available, this information can be compared and supplemented with the information from the direct examination of the patient. With this more comprehensive and accurate assessment of the patient's episodes and their severity through analytical computations, clinicians can individualize more effective and suitable treatments for the patient's illness(es) and also improve assessment of current treatments' efficacy. Typically, psychiatric patients' stresses are dynamic in nature. For example, a patient's stress can be due to: (1) progression of an existing mental disease/disorder; or (2) a patient's thoughts and behavior provoked/initiated by (a) interactions with family members and friends, (b) information gathered from internet sources, TV shows; entertainment media, or (c) from unpleasant incidents or volatile internal thought processes.

Real-time observations and analysis by trained clinicians of their patients' behavior, speech, and facial expressions are invaluable and critical to a better diagnosis and treatment of patients, since this provides more accurate information on symptoms and disease progression (i.e., improvement or deterioration of a patient's mental disease from the time of a previous clinical examination) Unfortunately, in most cases, this real-time dynamic patient information is not available, as patients may experience psychological stresses and distress at any time in their daily lives, and not necessarily while they are with their clinicians.

FIG. 1 illustrates stimuli interactions with relevant main components of brain structure, nervous system responses and biometric sensors' data capture flow chart that provides an overview of the system and a method for collecting objective assurements of different biometric parameters in real time. Different types of stimuli 1002 can be given to the patient and processed through the different sensory organs of the patient 1004 such as visual, aural with patient oral responses, kinesthetic interactions etc. In this system two types of stimuli, namely Standardized Stimuli and Structured Stimuli are the inputs administered in clinical environment by trained clinical personnel or in a standardized controlled environment. Standardized Stimuli are defined hereafter as the questions from standardized psychometric tests, physical tasks to test dexterities, cognition etc. and selected by the clinicians pertinent to patient condition. Structured Stimuli are defined hereafter as the questions to the patient in physicians' patient examination to evoke patient responses as part of differential diagnostic procedure to arrive in patient's illness prognosis. These stimuli can be questions, playing video games, or responding with verbal and task oriented computations for financial, cognition, physical dexterity measuring inputs. Other aspects of the invention relate to stimuli experienced by the individual that are completely unscheduled, unforeseen, unplanned or unintended, for example, anxiety moments or episodes, depressive periods or times in a day, unanticipated triggering events, traumatic or catastrophic events away from clinical settings. The figure further depicts different parts of the brain that processes the stimuli to induce somatic and autonomic nervous system reactions 1016.

The patient's various autonomic physiological parameters (APPs) will respond and react to the induced stimuli. By utilizing biometric devices 1018, these APPs can be detected with far more precision and accuracy than is feasible through a clinician's simultaneous visual observations. Some of the APPs captured by the biometric devices include blood pressure, electrical bio-signals of the brain, heart and pulse rate, breathing rate, breathing volume, perspiration and sweat textures on face, skin conductance, eye movements, facial changes including color & texture changes, posture changes, muscle movements (voluntary and involuntary), and speech and tonal changes, as applicable. These biometric parameters can capture changes and severity of individual patient's feelings, emotions 1014 and theft innate resiliencies, coping skills, (healthy) behavior, function and responses 1012. From the biometric devices, the data sets 1020 created will be provided in near real time to the clinician that will be compared to a master database of the patient's previous sessions and other patients with comparable illness conditions.

A patient's recall from memory of an episode and stress experiences, though valuable, is not entirely accurate, due to its static nature. Actual episode events and a patient's reactions in real-time are modified during recall in the clinician's office examination in intensity and duration, caused by the patient's coping mechanisms. The clinical treatment objective of using therapy and medications is to enhance coping skills in a patient. These moderating coping mechanisms can invoke a modified and coped history of a stress episode/event from a patient's recall at a later time. Physicians, at present, do not have a record of an actual event to infer the event intensity or severity measurements Stresses generate dynamic nervous system responses during an episode's occurrence. Biometric records and analytics of the actual event and a recording of the real-time description and responses by the patient as the episode continues, can provide a trained clinician with superior information about the patient's progress and mental health status. Currently, unless a patient is going through a major mental health episode at the time of a pre-scheduled clinical examination appointment; or a patient is in emergency care and being examined; or the clinician selectively induces certain mental health conditions, a patient's account of recalled prior events is the main source of this information to the clinician, This objective record of patient's biometric reactions can help in improved diagnosis, treatment plan design, and monitoring. A quantifiable and objective patient record providing an additional basis for medications choice, dosages, treatments design and changes corresponding to patient progress, will also assist in reducing the clinician's legal liability. Patients can be shown as a review and feedback visually-quantifiable changes between successive office visits or different stress episodes of their progress and results from modifications to treatment plans (therapy and medications) to motivate towards positive behavioral health progress.

Figure 8:
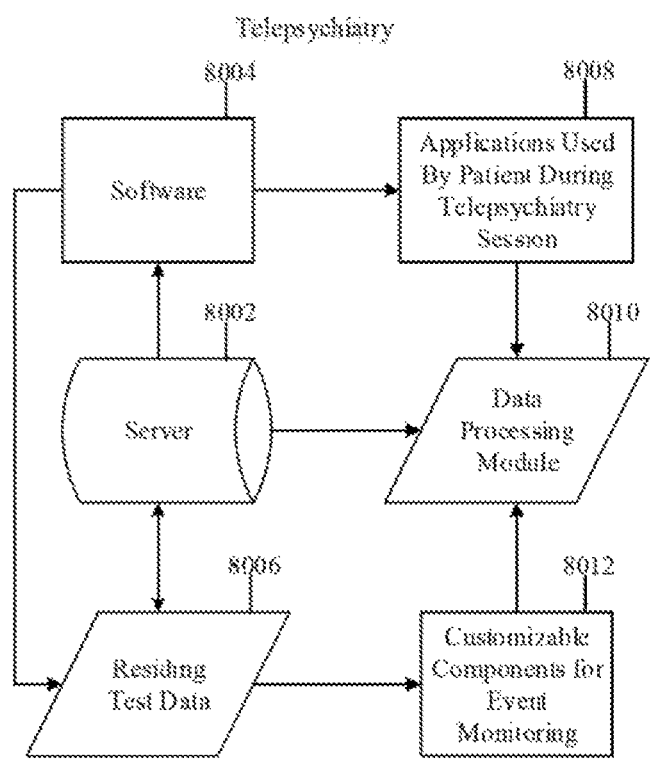
FIG. 8 is a block diagram depicting the telepsychiatry component of the system.

It will also enhance the current telepsychiatry practices, as shown in FIG. 8. The system may be internal or external cloud-based server application 8002 with software 8004 controlling the user experience and user interface for the patient and user controls with a different user experience and user interface for the clinicians. The applications including residing test hank data 8006 can reside within the software package or be retreated from the server to be utilized during a telepsychiatry session 8008. The test bank data can utilize customizable components configurable by the clinician for each individual patient tailored for specific illness and the patient's event monitoring 8012. The patient response data from the testing, applications during the telepsychiatry sessions, clinician office examinations, other customizable components and clinician assessments go through a data processing module 8010 to be viewed on the clinician's user interface and sent to the server for later retrieval and patient profile.

At present, telepsychiatry practices utilize commercially-available, internet-based video-conferencing tools. Many of these current systems do not have the required medical device standards of calibration protocols and processes. There are significant observational and inferential differences between a patient being directly examined by a clinician at his office and the two-dimensional pictures transmitted by internet due to many factors, such as: occasional transmission lags, changes in speech and tone qualities from microphone specification and precision variations, bandwidth changes during real time interaction of patient and clinician, signal compression variations among different suppliers of commercial systems, and patients turning away their face and eyes at times from the recording camera. Real-time analytics of patient APPs captured through biometric devices provided by the present invention will help the clinicians by improving the quality of telepsychiatry patients' clinical examination processes and incorporation of relevant calibration and testing protocols and standards.

Psychiatry practice currently utilizes minimal objective inputs (i.e., biometric parameter changes) for a patient during an exam, or over a treatment period. Although drug studies are standard for FDA approval for physical illnesses, there are very few studies, objective evaluations, or measurements of treatment plans combining medicines and therapies in behavioral health care. In mental health care, treatment with medication is often integrated with psychotherapy, rehabilitation or community-based support services. These are all integral components of contemporary mental health treatment. Application of the methodology described herein to assess a patient's progress from integrated medications and therapy treatment plans is made possible by recent advances in digital communications, cloud computing, mobile applications linking with biometric devices, ease of connectivity, and consumers' widespread use of these technologies. Essential mathematical tools in pattern recognition, multi-dimensional dynamic modeling techniques, algorithms to compute large volumes of data locally at the user location, and cloud technology to integrate and process relevant information in real-time have not been available or feasible until recently.

Figure 3:
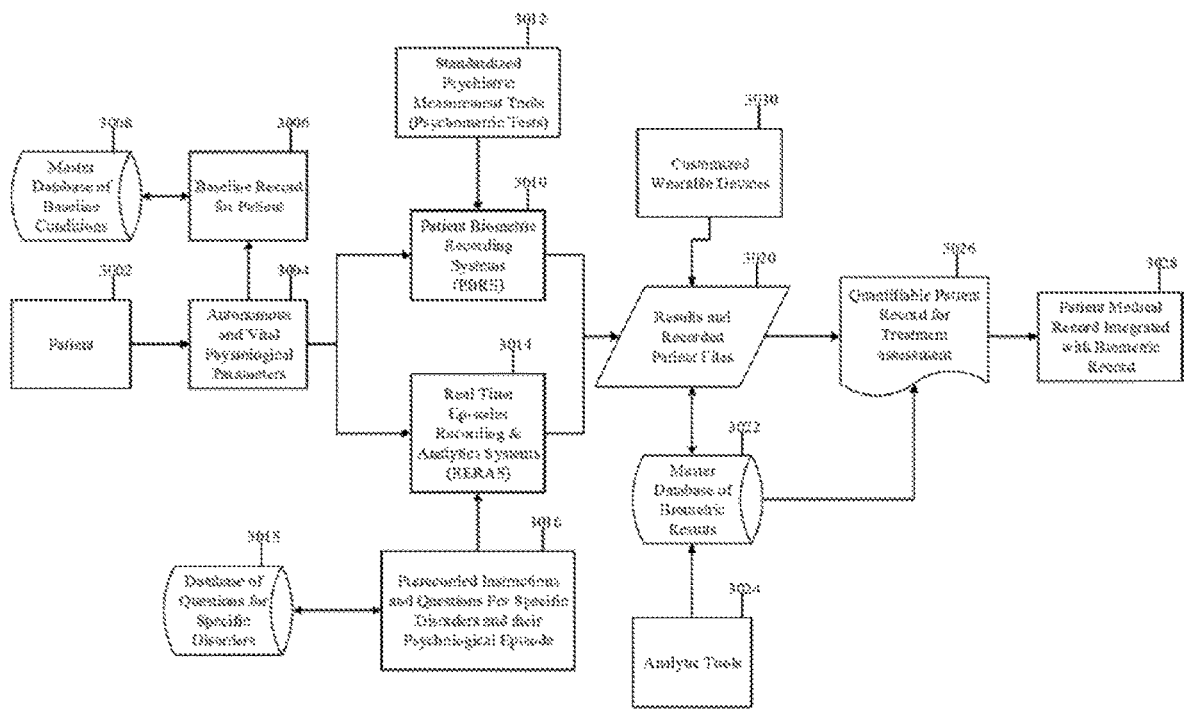
FIG. 3 is a block diagram depicting an integrated, real-time-biometric recording, monitoring, and information-analytics system configured in accordance with an embodiment of the invention.

Two hardware systems (Patient Biometric Recording Systems, "PBRS"; and Real Time Episodes Recording & Analytics Systems, "RERAS") with different biometric devices and video cameras, optionally attached for data capture, are chosen by the clinician, as depicted by the system in FIG. 3. These systems have pairs of video (visible spectrum) and thermal infrared (IR) video camera subsystems to capture facial features, pupil size changes, eyelid flutter rates, perspiration, and facial blood flow changes; and record speech with different levels of sensitivity, precision and specifications. PBRS and RERAS are integrated multi-sensor systems employing the necessary image, audio, digital and analog sensor data fusion techniques and tools. Vital physiological parameter measurement devices for monitoring blood pressure, pulse rate, skin conductivity, breathing rate, bloody oxygenation levels, and/or temperature are designed to be connected to the system with Bluetooth and/or WiFi communication capability, Clinicians can use the first system, PBRS and its variants, as necessitated by the illness and diagnostic requirements, in their office to record a patient's biometric changes during their patient examination and administration of standardized psychiatric measurement tools (e.g., psychometric tests). Examples of some of the commonly used psychometric measurement tools are listed in Tables 1-7. As newer tests and digital tools, such as video games, brain exercises, focus enhancing aids (e.g. sensation of movement or strain in muscles, tendons and joints like prayer beads, squeeze or stress balls and objects) to test and improve memory, cognition, reasoning, speed of processing, financial skills in elderly, attention deficit etc., are accepted into clinical protocols and use, these will be integrated with our Standardized Stimuli Tests database used by the clinicians to select appropriate tests.

TABLE 1

Common Psychometric Measurements and Tests

| Name of Test | Summary |
|---|---|
| Psychiatric Mental Status Examination (MSE) | Obtains a comprehensive cross-sectional description of the patients mental state, which, when combined with the biographical and historical information of the psychiatric history, allows the clinician to make an accurate diagnosis and formulation for a coherent treatment plan<br>Data is collected through a combination of direct and indirect means: unstructured observation while obtaining the biographical and social information, focused questions about current symptoms, and formalized psychological tests<br>Six major sections of the MSE:<br>Appearance, Attitude, Activity<br>Mood and Affect<br>Speech and Language<br>Thought Content, Thought Process, and Perception<br>Cognition<br>Insight and Judgment |
| Mini-mental state examination (MMSE) or Foistein Test | Brief 30-point questionnaire test that is used to screen for cognitive impairment<br>Commonly used in medicine to screen for dementia<br>Used to estimate the severity of cognitive impairment and to follow the course of cognitive changes in an individual over time, thus making it an effective way to document an individual's response to treatment<br>Taking 10 minutes, it samples functions including arithmetic, memory and orientation. |
| The General Practitioner Assessment of Cognition (GPCOG) | Brief screening test for cognitive impairment introduced by Brodaty el al, in 2002<br>Specifically developed for the use in the primary care setting |
| MMPI-2: Assessing Personality and Psychopathology | Most widely used personality test in the U.S. and around the world<br>Employed in mental health settings, medical centers, and correctional programs, and is frequently admitted as evidence in legal proceedings<br>Used in screening applicants for jobs that involve public trust and safety |
| The Personality Assessment Inventory (PAI) | Provides critical information for psychologists about a client's psychopathology and constructs for effective treatment |

TABLE 2

Mental Disorders Specific Measurement Tools (Depression)

| Name of Test | Summary | Administered by | Length of Time |
|---|---|---|---|
| Patient Health Questionnaires 2 and 9 (PHQ-2 and PHQ-9) | Designed to screen (detect), diagnose, monitor and measure the severity of depression | Self-reported or clinician-administered | 5 to 10 minutes |
| Beck depression inventory (BDI-II) | Assess the existence and severity of depressive symptoms | Self-reported or clinician-administered | 5 to 10 minutes |
| Hamilton rating scale for depression (HAM-D) | Assesses the severity of and change in depressive symptoms | Clinician-administered | 20 to 30 minutes |
| Montgomery-Asberg Depression Rating Scale (MADRS) | Measures the degree of severity of depressive symptoms, and as a sensitive measure of change in symptom severity during the treatment of depression | Clinician-administered | 15 minutes |
| Major Depression Inventory (MDI) | Assesses the presence and severity of depressive symptoms | Self-report scale | 5 to 10 minutes |

TABLE 3

Mental Disorders Specific Measurement Tools (PTSD and ASD)

| Name of Test | Summary | Administered by | Length of Time |
|---|---|---|---|
| Davidson Trauma Scale (DTS) | Provide a quick measure of posttraumatic stress disorder (PTSD) symptoms | Self-rating scale that can be used with both individuals and groups | 10 minutes |
| Clinician-Administered PTSD Scale (CAPS) | Used as the standard in PTSD assessment | Administered by clinicians, clinical researchers and trained clinical assistants | 45 to 60 minutes |
| PTSD Checklist (PCL-M and PCL-C: Military and Civilian Versions) | Screens individuals for PTSD, diagnosing PTSD, and monitoring symptom change during and after treatment | Self-report scale that consists of 3 versions: military version, civilian version, and a specific-event version. | 5 to 10 minutes |
| Acute Stress Disorder Interview (ASDI) | A structure interview for clinicians to diagnose ASD | Trained individual | 5 to 10 minutes |
| Acute Stress Disorder Scale (ASDS) | Self-report version of the Acute Stress Disorder Interview (ASDI) | Self-report | 5 to 10 minutes |

TABLE 4

Mental Disorders Specific Measurement Tools (Obsessive-Compulsive Disorder)

| Name of Test | Summary | Administered by | Length of Time |
|---|---|---|---|
| Yale-Brown Obsessive Compulsive Scale (Y-BOCS) | Rate the type and severity of symptoms in persons with obsessive-compulsive disorder | Given as an interview scale | 20 minutes |
| Leyton Obsessional Inventory (LOI) | Assess obsessional symptoms | 69 yes/no items that measure symptoms and traits | 15 to 30 minutes |
| Obsessive-Compulsive Inventory (OCI) | Measures the frequency of a broad range of obsessions and compulsions and their associated distress | Self-administered scale | 15 minutes |

TABLE 5

Mental Disorders Specific Measurement Tools (Panic Disorder)

| Name of Test | Summary | Administered by | Length of Time |
|---|---|---|---|
| Panic Disorder Severity Scale (PDSS) | Simple way of measuring the overall severity of a DSM-IV-diagnosed panic disorder | Clinician-administered | 5 to 10 minutes |
| Panic and Agoraphobia Scale | Assess the severity of panic disorder, with or without agoraphobia. It was also developed for monitoring the effectiveness of drug treatment and psychological therapy | Clinician-administered or self-rated | 5 to 10 minutes |

TABLE 6

Mental Disorders Specific Measurement Tools (Generalized Anxiety Disorder)

| Name of Test | Summary | Administered by | Length of Time |
|---|---|---|---|
| Hamilton Anxiety Scale (HAM-A) | Assess the severity of general symptoms of anxiety | Clinician-administered | 10 to 15 minutes |
| Beck Anxiety Inventory (BAI) | Measure the severity of symptoms of anxiety | Self-administered or administered verbally by a trained administer | 5 to 10 minutes |
| Zung Rating Scale for Anxiety | Measure of anxiety in general populations | Self-report | 5 to 10 minutes |
| Generalized Anxiety Disorder-7 (GAD-7) | Developed as a screen to detect generalized anxiety disorder | Self-report and clinician administered | 5 to 10 minutes |

TABLE 7

Mental Disorders Specific Measurement Tools (Personality Disorders)

| Name of Test | Summary | Administered by | Length of Time |
|---|---|---|---|
| Zanarini Rating Scale for Borderline Personality Disorder (ZAN-BPD) | Assess the severity of DSM-IV-based borderline symptoms | Clinician-administered | 1 week time frame |
| Mclean Screening Instrument for Borderline Personality Disorder (MSI-BPD) | Screening in groups of people to detect borderline personality disorder | Self-report screen | 5 to 10 minutes |
| Standardized Assessment of Personality-Abbreviated Scale (SAPAS) | General screen for personality disorders | Clinician interview scale | About 2 minutes |
| Iowa Personality Disorder Screen (IPDS) | Screen for personality disorders | Clinician-administered | 5 to 10 minutes |

The patients are given the second type of system, RERAS and its variants as necessitated by the illness and diagnostic requirements, to record a mental health episode as and when they experience one. The clinician can pre-record and load into RERAS customized instructions and specific questions with pauses, played to the patient when he initiates a recording session while experiencing a stress episode or attack. For example, in the case of ADD/ADHD, these sessions may include verbal and quantitative problem solving exercises selected by the clinicians, as suitable for the patient's age and academic background. These sessions may be designed and recommended to be administered at different times of the day to assess a patient's focus and attention spans impacted by sleep patterns and medication absorption and timed release effects.

Current common treatment protocols as per National Resource Center for ADHD include the following features: "Medication does not cure ADHD; when effective, it alleviates ADHD symptoms during the time it is active. After reviewing the scientific evidence, the AMA reported that 'pharmacotherapy, particularly stimulants, has been extensively studied. Medication alone generally provides significant short-term symptomatic and academic improvement and the risk-benefit ratio of stimulant treatment in ADHD must be evaluated and monitored on an ongoing basis in each case.' Common psycho-stimulant edications used in the treatment of ADHD are now available as both short- and long-acting preparations. There can be wide individual variation that cannot be predicted and will only become evident once the medication is tried. The specific dose and timing of medication must be determined for each individual. In addition, the individual is monitored and observed (for children, by parents and teachers) both on and off the medication. In all cases, the appropriate dose must be tailored to the individual patient and monitored by the prescribing medical professional to make any needed adjustments. The medication trial should be monitored very carefully, especially in the early weeks of treatment, so needed adjustments can be made to dose and timing. If the first medication tried is not helpful or produces unpleasant side effects, the prescribing professional will probably make adjustments. Medication treatment without monitoring, appropriate education about ADHD, and other appropriate treatment interventions is often not enough to help."

The objective, comprehensive and accurate information generated in different settings and timings generated by PBRS and RERAS addresses many of the real world shortcomings in the collection and analysis of patient behavior and function observations in varied settings, and improve the treatment of other mental illnesses as described for ADHD. Another variant of RERAS is a wearable multi-sensor data fused device designed to monitor and record patients' vital parameters, sleep patterns and patient reported changes in their daily life patterns over a specific time period. This device has the ability to monitor continuously some or all the parameters selected and configured by the physician and alert the patients when certain predetermined thresholds for these monitored parameters are exceeded by linking the wearable RERAS to portable devices, such as, smartphones, tablets and other computing devices. Physicians can recommend and train patients to speak and record their thoughts, answer sets of pre-recorded questions and record their facial expressions to a RERAS device or to their smartphones, tablets and other available devices. This invention subsystems, variants of sensor data fused devices, and contents are selected by the clinicians for each patient and illness.

The advances of the last 75 years in laboratory medicine and imaging transformed other major medical specialties and fields by enabling physicians to blend the metadata information from evidence-based clinical practices and drug trials with personalized medicine to treat individual patients. Mental healthcare does not have similar practices and protocols due to absence of objective measurements and aggregation of necessary threshold of patient condition variation information sets. Our systems will create and provide real time evidence-based measurable and objective inter- and intra-patient longitudinal information to the physicians in mental healthcare for the first time. This facilitates the primary care physicians and specialists to employ protocols and patient treatment practices for mental health similar to other medical fields and physical illnesses.

The initial patient examination and testing are used to establish a patient's baseline biometric record employing PBRS, if the clinician (physician or psychologist) determines to utilize biometric systems. Some of these psychometric measurements/tests are typically administered by psychiatric/mental health nurse practitioners, physician assistants, mental health psychotherapists, or psychologists (either in the clinician's offices or standalone testing centers as prescribed by the clinicians). These mental health examination and measurement tools are administered by text and speech modes through digitized format with natural or neutral tones and voice, as needed and determined by the clinicians. The patients will answer these questions only through verbal responses. PBRS captures patient verbal responses from physician office examination and psychometric testing sessions using a speech to text recognition software. The content of the speech will be analyzed and matched with similar questions from different office examination visits and testing sessions. Specialized search algorithms, speech and language functional analysis, and linguistic analysis tools such as LIWC (Linguistic Inquiry and Word Count) will be used in real time to collect idioms and words used by a patient to express different emotions, and positive and negative thoughts characteristic to him/her. By collecting and counting these words and expressions, frequency tables of positive and negative emotions and thoughts for different sessions are developed. The software will also match these words with internally developed dictionaries of group of words classified into various classes that express strong, moderate and mild levels of six basic emotions and related thoughts. The changes in the frequency and intensity of these words and expressions are shown in comparative graphical and tabular formats to the clinician. An increasing trend in positive emotions and word expressions evidences an improvement in patient's coping skills and illness progress. Increasing trend in negative emotions and expressive words evidences deterioration. Absence of significant changes between successive patient examinations and testing sessions evidences 'no major change' in patient's coping skills and illness.

The combination of APP changes and LIWC analytics will assist in early detection and differentiation among mental illnesses. This invention integrates findings from a number of research studies that typically identify one or few differentiating features, that increase reliability in diagnosis and patient monitoring. For example, linguistic analysis programs have features to record a patient's patterns of vowel-spacing (known as vowel-space ratios) compared to healthy participants. These linguistic tools when combined with patient length and shortness of smiles, frequency of looking away and looking to the ground (from facial expression changes and camera recordings of patient examination, testing and stress event real time episodes) will increase differential inferential power to diagnose depressions at earlier stages. The APP analytics from standardized patient tests, specified activities or exercises and real time episode events, and speech and language functional analysis are combined to analyze irritability and fatigue versus racing thoughts and extreme energy; risky behaviors; sleep, weight and appetite changes etc. to assist physicians in differentiating depressions, bipolar disorder and other illnesses. These new systems and tools monitor and record patient responses for longer periods and daily activities than a clinician is able to observe. A physician can utilize this improved specificity with other relevant patient information like genetic risk factors, blood tests, relevant pharmacogenomic tests, brain scans, other physical illnesses etc. to select better therapies.

Additionally, clinicians utilize these systems to assess treatment efficacies, conventional and non-conventional therapies like brain stimulation, power of prayer, meditation; music therapies, yoga, music etc. and other personalized therapies.

The combination of the biometric sensor integrated devices' data fusion summary information and the patient speech and language functional analysis are the two crucial features of the 'expert systems' design of this invention. Experienced and trained physicians and specialists observe patient's reactions, behavior and cognition and analyze the contents of responses to their questions in their patient examination. These expert systems quantify this relevant information generated during this process and develop inter and intra-patient longitudinal information for different mental illnesses. Averages for different severity levels (e.g. five different levels representing extreme, high, average, moderate, mild level of each mental illness type) and conditions of different illnesses from the physicians' diagnosis and the matching quantified data are components of the database progressively developed by our system. This database is aggregated and used for computations to develop average values, deviations from averages and spread measures for different severity levels and illnesses. Patient progress is assessed from the significant changes in the biometric, and speech and language functions.

Figure 4:
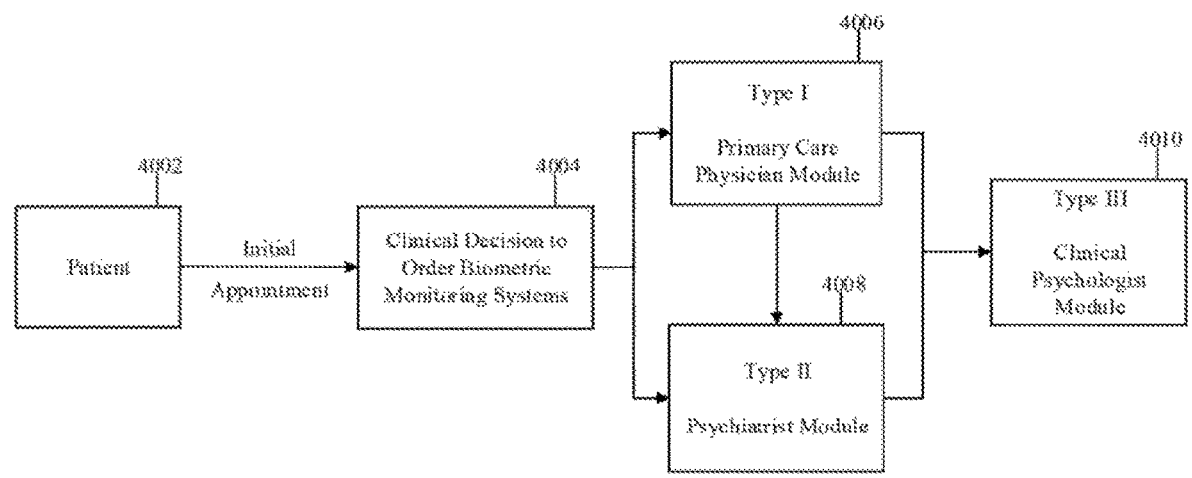
FIG. 4 is a block diagram depicting a clinical decision to order 1-2 types of biometric monitoring systems based on an initial appointment with a patient.

FIG. 4 is a block diagram depicting a clinician decision to order biometric monitoring systems in the initial patient evaluation. Typically, patients' initial clinical examination, diagnosis and treatments are performed by their primary care physicians. When the patient 4002 sets an initial appointment with their primary care physician or is referred to a specialist, the clinician attending will make the decision to utilize the biometric monitoring system 4004. By default, the primary care physician will be able to select a module 4006 specific for the primary care physician. If the patient went to see a psychiatrist or specialist first, the clinician will select a module 4008 specific for psychiatrists. Based upon the feedback and results for the psychiatrist and primary care physician's module, they may refer the patient to psychologists or use a modified psychologist module 4010 for initial screening and testing.

FIG. 3 is a block diagram depicting a clinical decision to order one or more types of biometric monitoring systems based on an initial appointment with a patient. Using our system, the patient 3002 will have their autonomous and vital physiological parameters sensor data 3004 captured. The clinician will create a baseline record for the patient 3006 to be processed by a master database of baseline conditions and parameters 3008 for defined thresholds and baseline records. The APPs captured by the two systems configurable by the clinicians, as needed, for specific purposes for their patients: Patient Biometric Recording Systems (PBRS) 3010 and Real Time Episodes Recording and Analytics Systems (RERAS) 3014. For the PBRS system, clinicians employ the system in a controlled clinical setting and APPs of the patient can be captured during standardized psychiatric measurement tools (psychometric tests), patient examination process and other standardized sessions 3012.

For the RERAS system, pre-recorded instructions and questions for specific disorders and their psychological episodes are loaded by the clinician based upon specific disorders or diagnosis 3016. These sessions are retrieved from a database of questions for a specific disorder and updated or retrieved, as needed. Additional customized wearable devices, another component of RERAS and PBRS systems can be ordered by the clinician for additional monitoring such as sleep monitoring and other physiological parameters 3030. The resulting patient data from the RERAS and PBRS system will be recorded 3020 and sent to a master database of biometric results 3022. The database or systems will have analytic tools 3024 to process the biometric results in real time to process and deliver the resulting quantifiable patient records for treatment assessment to the clinician 3026. These patient records can be integrated with the other patient medical records and are designed to be compliant with the necessary HIPAA regulations 3028.

Figure 5:
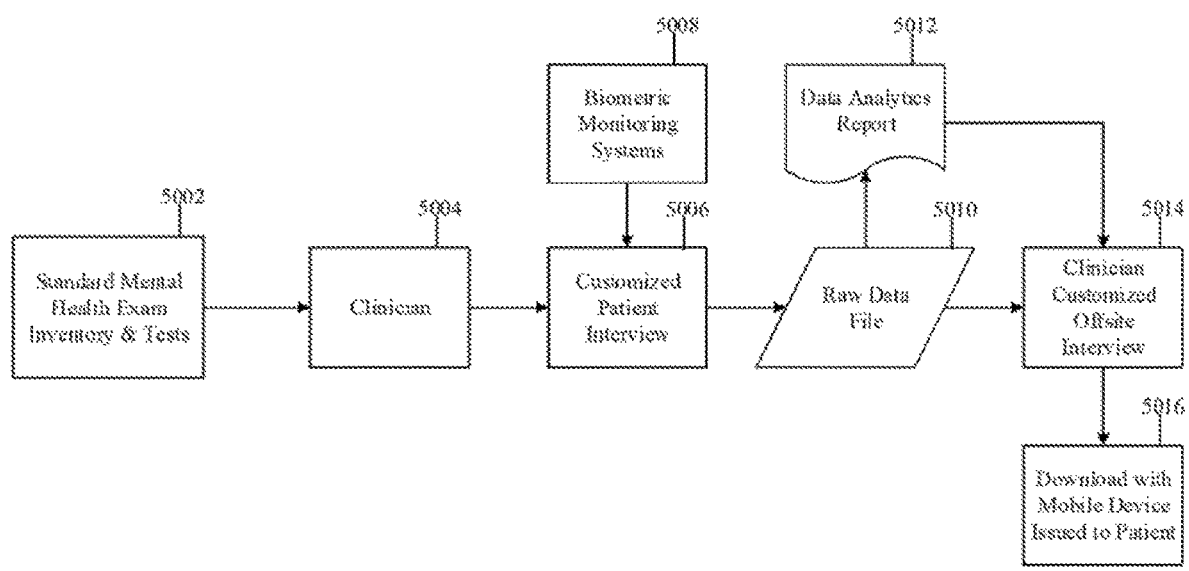
FIG. 5 is a block diagram depicting a clinician's interaction with the biometric system and the associated data analytics report of the patient.

FIG. 5 is a block diagram depicting a physician's assessment/diagnosis. This figure shows specialist referral to a psychiatrist or therapy sessions to be red by clinical psychologists based on standard, mental-health inventory data and other illness specific psychometric tests supplemented with baseline, biometric-monitoring-system data acquired during the patient examination Standardized mental health exam inventory and tests 5002 are selected by the clinician 5004 to be used in a customized patient interview 5006. The biometric monitoring systems 5008 is utilized during the patient interview to capture raw APP and speech and language data 5010 and processed into a data analytics report 5012. The clinician can create customized offsite interviews and sessions that can be downloaded on a mobile device (RERAS) issued to the patient 5016 for additional illness specific testing.

The clinician decides (based on the analytic results of the initial office session) the format, questions, and any mini-therapy sessions to be activated and recorded by the patient as a part of the real time episode recording session. This personalized pre-recorded session is loaded into RERAS and can also be downloaded into a smartphone, tablet, laptop or hardware device. RERAS is linked to a patient's smartphone through an application (custom developed and integrated) to assist with RERAS to focus on the face for optimum recording quality adjusted for ambient lighting conditions. The phone application has the ability to communicate and transfer the recording files from RERAS to clinicians and a main server in real-time.

Figure 2:
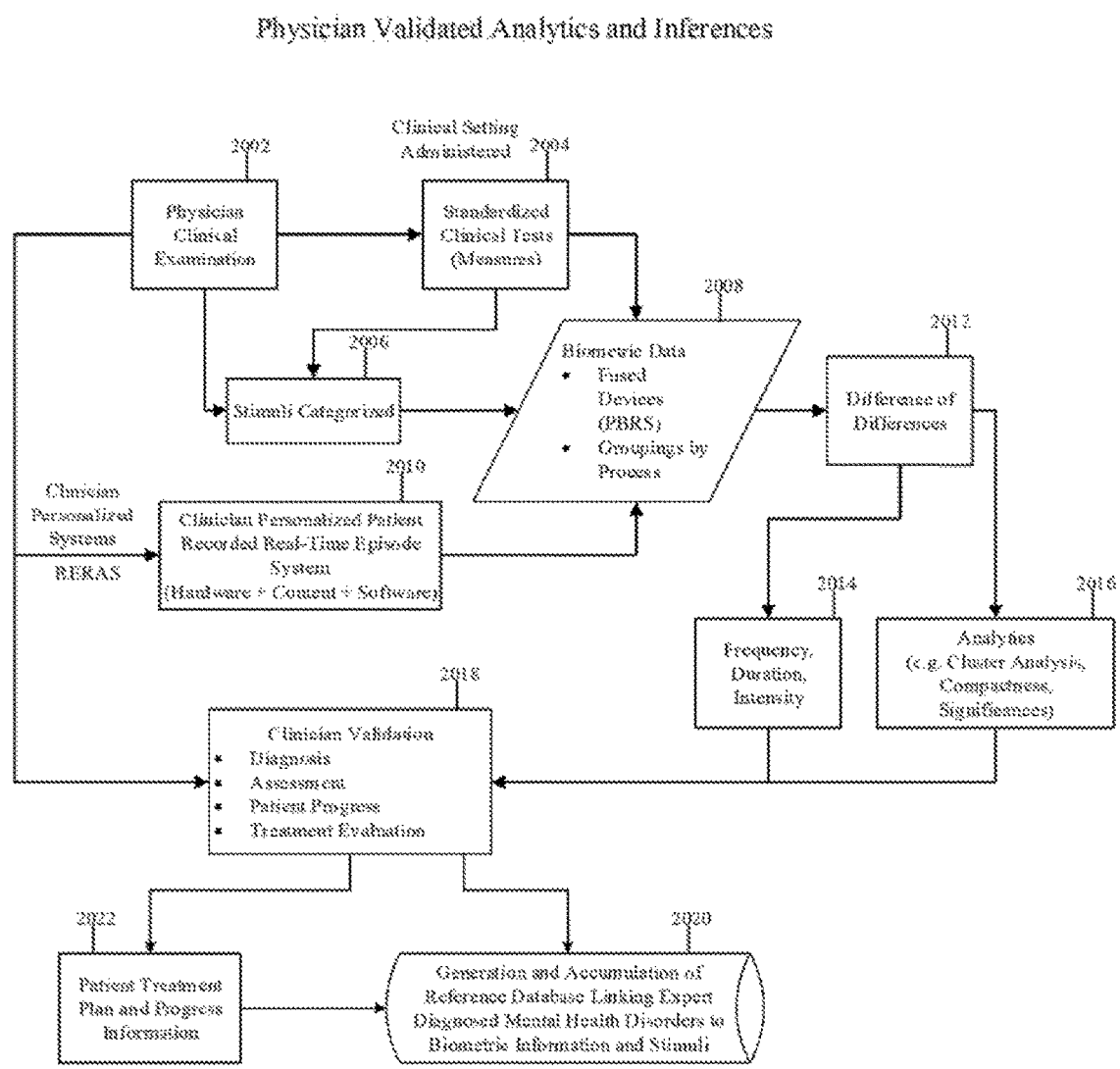
FIG. 2 is a block diagram depicting a physician-validated, analytics/inferences system in accordance with an embodiment of the invention.

As depicted in FIG. 2, the present invention provides biometric tools to acquire, analyze, and interpret objective measurable data related to a patient's mental disorder (in addition to data from the usual measurement tools administered) while a patient is answering questions during an examination. During a physician or clinician's clinical examination 2002 in a clinical setting, standardized clinical tests (or measures) 2004 are administered with controlled stimuli that are selected suitably from categories relevant for the patient illness 2006. During these standardized tests and sessions, biometric devices and systems capture different APP data grouped together in various types (analog signals, digital signals, video data, raw or processed image files, or linguistic text captured from the patient oral responses). The physician can also configure for remote monitoring (RERAS) to record real time events precipitated randomly or with known triggers by fully integrated hardware to capture selected APPs 2010 that can integrate into the PBRS system or independently to a cloud server, if required.

The two systems, PBRS and RERAS, capture and compute the difference of differences for the different APPs 2012 captured. The system will detect the frequency, duration and intensity changes for each of the differences 2014 and perform sequential analytics on the raw data such as cluster analysis, compactness, and identify significant observations and variations 2016. This information will be presented to the clinician as a part of increased specificity to help in improved diagnosis, prognosis, evaluation of prior treatments, and monitor patient progress 2018. The physicians utilize the system's data to create a patient treatment plan and define objective metrics to assess patient progress 2022. This same information is collected to generate and accumulate a large reference database linking clinician inferences on patient mental health illness to biometric information and corresponding stimuli, to initiate and successively improve the machine learning algorithms and processes of the system. This process underlies the clinical validation component of the database 2020. The system further provides real-time episode recording, patient's feedback, APP data and analytics of the dynamic changes during an episode and integrates longer duration sleep and selected vital parameters' monitoring information from wearable device(s). This kind of information has not been available hitherto to clinicians to improve patient diagnosis, treatment and outcomes. This information can also be used as supportive evidence for FDA clinical trials of new medications for behavioral illnesses and other illnesses with mental stress comorbidities.

Analytical tools and algorithms perform computations and longitudinal analysis on the acquired data to present the length and intensity of the episode; changes in tone, speech patterns, facial and pupil changes, skin conductivity; and vital parameter (e.g., pulse rate, blood pressure, respiratory rate, or temperature) changes superimposed with time stamping to denote significant APP changes. Another output is a record of real-time, patient feedback of his/her thoughts during an episode rather than recall from memory—a coping mechanism filter. This can be compared with the recall during a previous office visit to assess the 'Changes in Coping Mechanisms and Skills' a patient is expected to develop from the treatment. This can also provide reports similar to EKG/EEG with significant deviations, changes, and change-of-changes between different sessions for the same patient, and among a population of patients grouped by different parameters such as gender, age, health condition, pre-existing general health conditions, and socio-economic backgrounds to assess and monitor a patient's progress.

Figure 7:
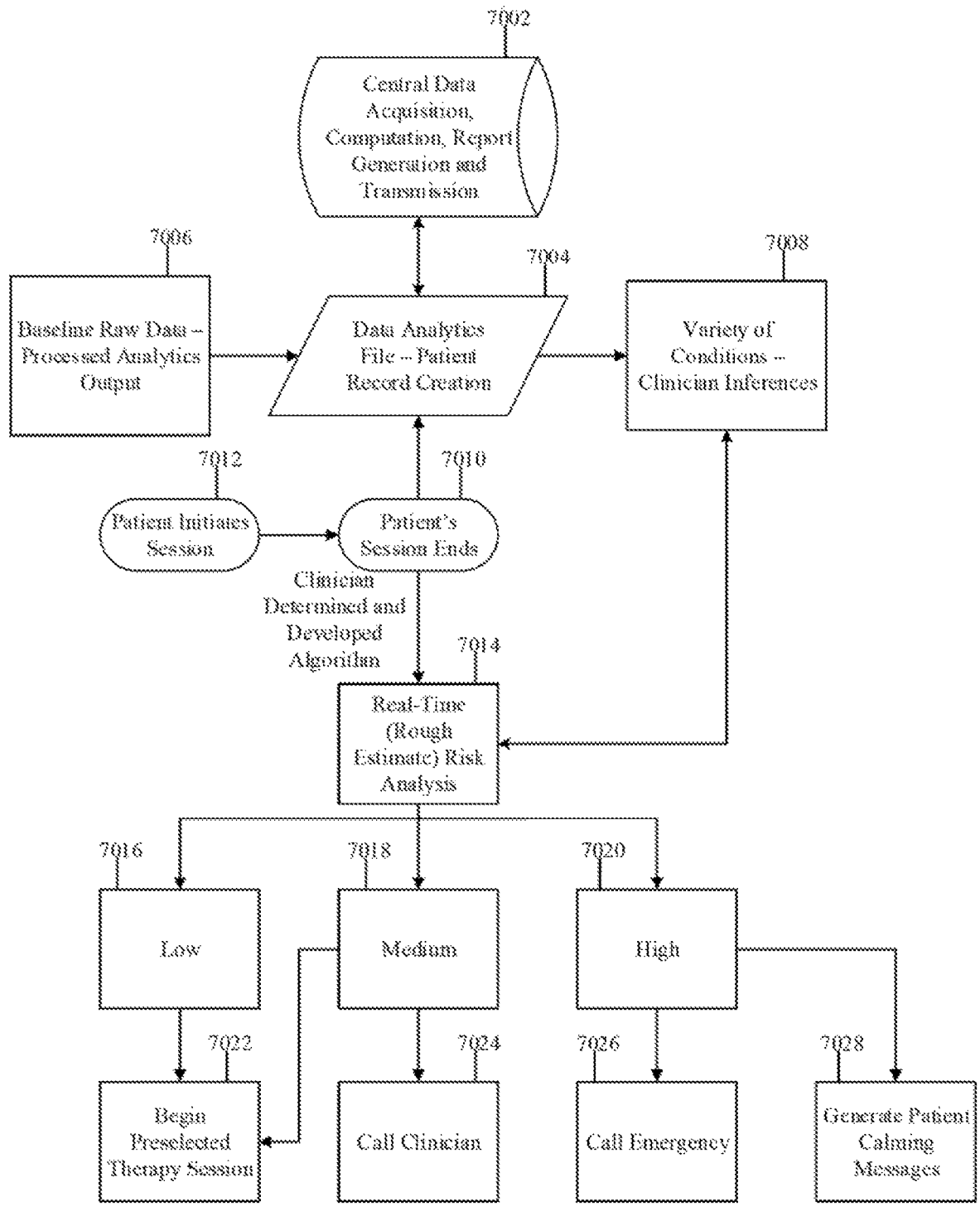
FIG. 7 is a block diagram depicting the risk analysis for a patient in the system.

The clinician has the flexibility to record a personalized (i.e., for each patient modified after each patient's office visit) set of mini-therapy sessions and, thereby, make them available to the patient as an off-site session based on real-time risk analysis and thresholds customized for each patient, as shown in FIG. 7. For a typical session 7012 the clinician can determine and specify sensors and the algorithms required for the patient's illness conditions to record an episode or a stress event 7010. During the recording session, the master database records of all prior patient APP measurements information of baseline information, patient other illnesses relevant data, prior real time events output reports are integrated and new information generated 7002 applying the data analytics 7004 on raw data 7006. The output can relate to a master database of known conditions and provide relevant longitudinal information to aid the clinician's diagnosis process 7008 along with a rough estimate for a real time risk analysis based on the patient analysis 7014.

The risk analysis component will categorize the patient condition into three categories: tow 7016, medium 7018, or high 7020. If the risk categorization is low, a personalized short therapy session created by the clinician is initiated 7022. For medium risk, the physician can pre-plan by programming a call to a friend or family member to provide support and assistance and another call to afterhours clinician consultation, if available, 7024, and begin a prior recorded therapy session as per the patient requirements 7022. If the risk categorization is high, emergency protocols 7026 are initiated by placing calls to emergency help, to patient immediate care and support providers to help the patient and begin playing calming messages based on each patient illness conditions as designed by the clinician. The session prerecorded contents, psychometric tests and measurements and biometric sensors programmed for recording are different for different type of illnesses. For example, in the application for ADD/ADHD patients, devices are programmed to record limb movement patterns.

The methodology described herein is useful for monitoring, stratification into different groups by severity levels, progression and changes in severity for each illness, and treatment assessment of many illnesses, such as, but not limited to: types of different anxieties, neurotic (dysthymic) depression, and other depressive disorders; attention deficit disorders; Post Traumatic Stress Disorder (PTSD); co-morbidity with other disease; addiction withdrawals; and psychiatric presentations, reactions, or complications from other major diseases, illnesses, medical treatments or surgeries, stress influenced conditions like Irritable Bowel Syndrome (MS), gynecological disorders etc., and for other illnesses as determined by the attending physicians.

Figure 6:
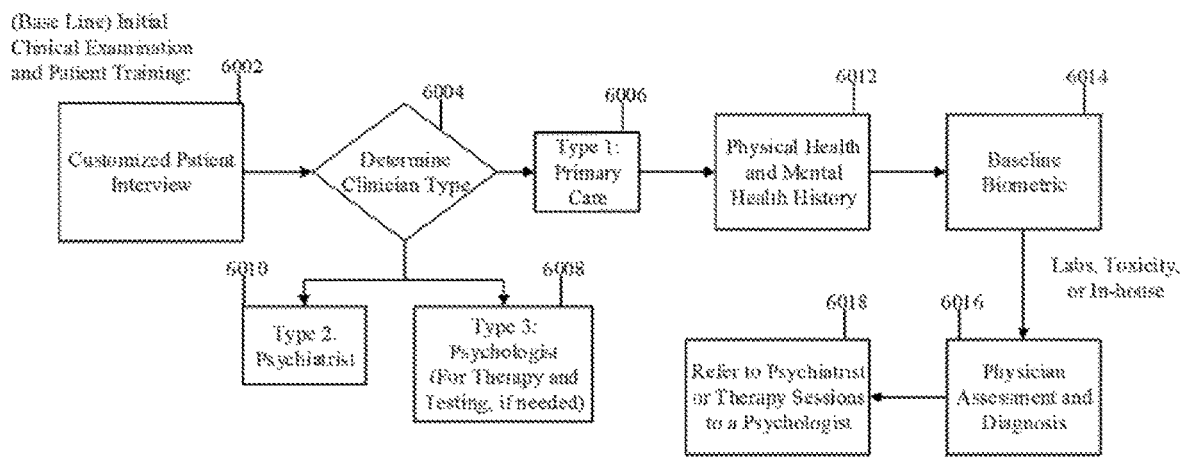
FIG. 6 is a block diagram depicting acquisition of a patient's baseline profile by labs or toxicity data, if needed, and referral to either a psychiatrist or psychologist for therapy.
Figure 9:
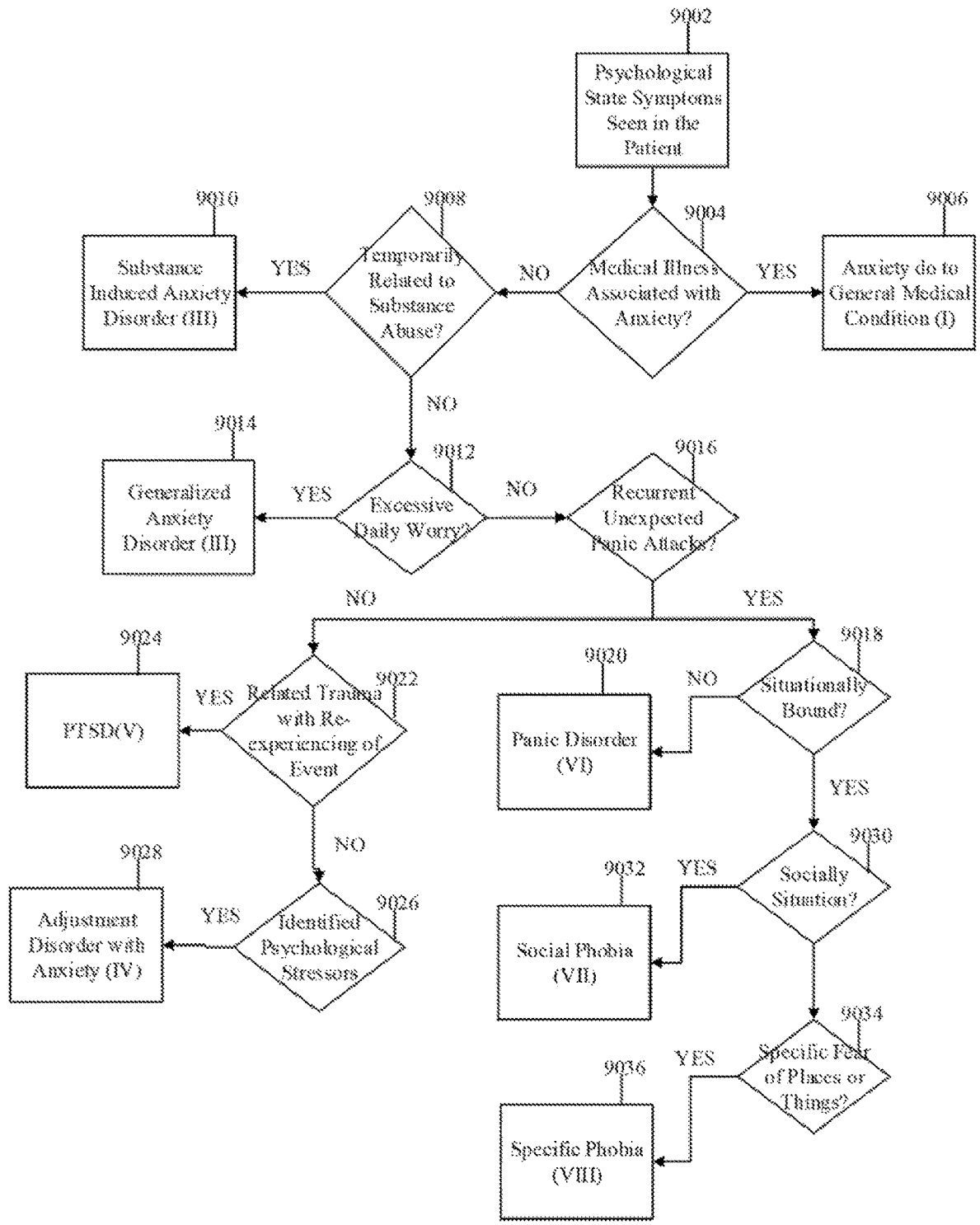
FIG. 9 is a block diagram depicting the diagnosis decision tree of specific disorders in patients exhibiting psychological state symptoms.

FIG. 9 is a flow chart depicting a diagnosis decision tree of certain specific disorders in a patient exhibiting psychological illness state symptoms. The clinician will see the psychological state symptoms in the patient 9002 and determine if the medical illness is associated with anxiety 9004. If the diagnosis is associated with an anxiety, the diagnosis may be a general medical condition 9006. If the diagnosis is not related to an anxiety, the next decision tree diagnosis is to determine if the medical illness is temporarily related to substance abuse 9008. If it is, the diagnosis is substance induced anxiety disorder 9010, if not the clinician will go to the next decision tree diagnosis option, an excessive daily worry 9012. If there appears to be symptoms related to daily worry, the diagnosis may be generalized anxiety disorder 9014, if not, the clinician will determine if the patient is having recurrent unexpected panic attacks 9016. If the patient's unexpected panic attacks are not recurring, the clinician will determine if these attacks are related to a trauma with re-experiencing of an event 9022, the diagnosis of the patient might be related to PTSD 9024 or if there are some identified psychological stressors 9026, the diagnosis may be adjustment disorder with anxiety 9028. If the patient is having recurrent unexpected panic attacks 9016, the clinician will determine if the patient is seeing symptoms evoked by specific individual situations or with any identifiable triggers 9018, panic attacks which could lead to a panic disorder diagnosis 9020, social situations causing the panic attacks 9030, for a social phobia 9032 diagnosis, or a specific fear of places or things causing the panic attack 9034 which can lead to a specific phobia 9036 diagnosis. Integrating with the results of this system's invention, differential diagnosis decision trees, such as those depicted in FIG. 9, can be developed and extended to include many types of behavioral health illnesses, illness severity level differences, monitoring patient progress protocols and illness management. For each patient, baseline conditions are tested and recorded to facilitate inter- and intra-patient longitudinal illness objective comparisons and measurements.

a. One approach for creating these patient objective baseline conditions and measurements by the suitable clinician type is depicted in FIG. 6. When initializing a baseline profile, clinicians customize the type of APPs and corresponding sensors of the devices for the objective data capture, psychometric test(s) and office examination protocols to each patient. The system will allow the clinician to initiate a clinical examination for a customized patient interview session 6002. Based on initial diagnosis, the clinician determines to accept this patient for treatment or to refer the patient to 6004 other specialist clinicians, psychiatrist 6010, psychologist (for therapy and psychometric testing, if needed) 6008, or primary care physician 6006. If the patient is treated by the primary care physician, the physician selects the biometric APPs testing to create patient base line condition profile based on the initial diagnosis. The primary care physician integrates patient's physical and mental health history 6012 and decides to employ the biometric measurement systems to create patient behavioral health baseline measurements 6014. The physician diagnoses and assesses with higher specificity patient's behavioral health condition and records baseline objective measurements as part of the patient medical records 6016.

b. if needed, results from additional relevant pharmacogenetic, toxicity and laboratory tests, and radiology imaging interpretations (that are currently available or shall become available in future and form part of the existing or new protocols) ordered are collected for further assessment of baseline and threshold patient profiles. These newer tests are helping the physicians to select more effective and appropriate medications for pre-existing health conditions and addictions. Some of these blood and laboratory tests include (relevant newer tests added after FDA approvals and protocol recommendations): pharmacogenetic tests, C-peptide, C-reactive protein, drug screening panel, erythrocyte sedimentation rate, ethanol, lactic acid, methadone, natriuretic peptide, opiates, procalcitonin, phenobarbital, testosterone, and total cortisol. By applying many of these tools and objective measurements, primary care physicians can improve current patient behavioral health care effectiveness and achieve better long-term patient health outcomes. Patients with complex, severe or chronic illnesses are referred by primary care physicians to a psychiatrist or specialized psychologists for the necessary therapy 6018.

The data acquisition devices, data processing techniques, measurement methodology, and information analytics to generate objective results and measurements information for the clinician are as described in published U.S. Patent Application US20130281798. Description of the data processing methodology and mathematical tools employed is detailed below. The ultimate goal is to build a capability to process large volumes of complex data into useful information to improve decision making processes by reducing the false alarm rates in diagnoses. These techniques are regularly applied by data scientists and expert systems' designers for data mining, big data processing, analytics, visualization and real time customer fulfillment areas and known to those proficient in the art

Data Analysis Tools: Pre-Processing

Anytime there are sensors and other modes of data collection, there are always calibration, biasing errors, noise and other sources of error to confront. This pre-processing step processes the data from all the sources of error information available. The output is the same data corrected for as many error sources as are known and feasible. The pre-processing step always involves conversion of analog sensor data to digital format.

II. Data Analysis Tools 1: Processing Step 1

This processing step consists of feature definition, feature extraction, feature selection, feature space reduction, and finally, use of the chosen features to perform cluster identification and classification. The classification data would then be used to derive instantaneous emotional responses' objective measurements and the mental state of the subject.

Feature Definitions

We define a set of features to extract from the data. For those pieces of data, which involve numerical data acquisition over periods of time, we construct (assuming M pieces of data $\{X_n\}$; to be processed)

a. Means
b. $\mu x = (1/M)\Sigma X_n$
c. Standard deviations
d. $\sigma x = [(1/(M-1))\Sigma(X_n - \mu x)2]^{1/2}$
e. Mean of First differences
f. $\delta x = (1/(M-1))\Sigma |X_{N+1} - X_N|$ For those acquisitions which involve time series of data, we perform a standard time series analysis, estimate power spectrum and identify characteristic frequencies at which large amplitudes occur. We then use, estimated frequencies and their amplitudes (absolute values) as features.

For those data acquisitions that involve specific event(s), such as response to stimuli, we classify responses to the features as, but not limited to: (1) indifference; (2) Joy/pleasure; (3) anger; (4) sadness/sorrow/tears/crying; (5) violent reactions. We classify these responses on a scale of intensity such as, 1-10 and categorize the subject accordingly. The number of features can be very large for every time interval chosen.

Feature Extraction

This involves processing each independent data set and extracting the features defined above. We denote the entire set of features collectively by the vector X. The ultimate goal is to map this feature vector to the mental state of the subject. Such mapping can be highly nonlinear. If we denote the mental state of the subject by the vector Y, then we look for a functional relationship of the form $Y=f(X)$. The next set of techniques address the inferences based on such nonlinear mapping to extract the mental state of the subject.

II. Data Analysis Tools 2: Clustering Tools

In a method called K-clustering, the entire feature set data can be converted into clusters. The method starts with a set of distinct K features. Treating these as centers, we map all the other features that occur around each of these feature centers. As the features get divided into clusters or emerging clusters, we redefine the centers of these clusters as the mapping indicates. At the end of the process, we have divided the feature data into clusters. It is quite possible that all the data will only form into one cluster, which will point to the fidelity of the data acquisition. If this occurs, the data acquisition and planning may have to be analyzed for correlationships, data spread and data behavior changes over different time periods, and in certain cases non-parametric relationships.

III. Data Analysis Tools 3: Principle Component Analysis

Principal component analysis (PCA) is a mathematical procedure that uses an orthogonal transformation to convert a set of observations of possibly correlated variables into a set of values of linearly uncorrelated variables called "principal components." The number of principal components is less than or equal to the number of original variables. This transformation is defined in such a way that the first principal component has the largest possible variance (that is) accounts for as much of the variability in the data as possible). Each succeeding component in turn has the highest variance possible under the constraint that it be orthogonal to (i.e., uncorrelated with) the preceding components. Principal components are guaranteed to be independent only if the data set is jointly normally distributed. PCA is sensitive to the relative scaling of the original variables. Depending on the field of application, it is also named the discrete Karhunen-Loeve transform (KLT), or proper orthogonal decomposition (POD).

The following is an example of the some of the details of the Principle component Analysis:

Step 1: Data on Feature Vectors $$\begin{bmatrix} \vec{x}_1 \\ \vec{x}_2 \\ \vdots \\ \vec{x}_K \end{bmatrix}$$

$\vec{x}_i = (x_{i1}, x_{i2}, x_{i3}, \ldots, x_{iM})$

Thus, there are M measurements on each feature measured.

Step 2: Compute the Mean

As before, compute the mean of each feature vector over the M measurements:

$$\mu_i = \frac{\sum_{j=1}^{M} x_{ij}}{M-1}$$

Step 3: Subtract Means from Data $\bar{y}_i = \vec{x}_i - \mu_i, i=1,2,\ldots K$

Step 4: Compute Covariance Matrix

Next compute the covariance matrix C in the feature space by $$C_{ij} = \frac{\sum_{k=1}^{M}(x_{ik}-\mu_i)(x_{jk}-\mu_j)}{M-1} (i,j)=1,2,\ldots,K$$

$$C = \frac{Y^T Y}{M-1}$$

$Y = X - h\Gamma^T$ $\Gamma = (\mu_1, \mu_2, \ldots \mu_K)$ where Y and X are (K×M) dimensional matrices, h is (K×1)) dimensional column of 1's and superscript T implies transpose of the matrix.

Step 5: Dianonalize the Covariance Matrix

Find the eigenvalues and eigenfunctions of the covariance matrix and order them in decreasing order of the eigenvalues (largest eigenvalue first and the next largest one and so on):

$\lambda_1 \geq \lambda_2 \geq \lambda_3 \ldots \geq \lambda_K$ $U = \bar{u}_1, \bar{u}_2, \ldots, \bar{u}_K)$ Where the $\lambda$'s are the eigenvalues and the $\bar{u}$'s are corresponding eigenvectors. Thus U is a K×M dimensional matrix with columns as eigenvectors.

Step 6: Reduce Dimensionality

Keep L eigenvalues and eigenvectors where L<K. We define a (K×L) matrix W by $W = (\bar{u}_1, \bar{u}_2, \ldots, \bar{u}_L) L<K$

Step 7: Normalize the Matrix Y

Normalize the matrix Y by $\sigma_i^2 = C_{ii} i=1,2,\ldots,K$ $\bar{\sigma} = (\sigma_1, \sigma_2, \ldots, \sigma_M)$ $H = (h \cdot \sigma^T)$ $b_{ij} = Y_{ij}/H_{ij}$ $B = (b_{ij})$

Step 8: Transform the B Data to the New Basis $Z = W^T B$

A number of algorithms are available to adapt for varied uses, data volumes and data behaviors in practice. These are adapted to the present context appropriately. PCA is a popular, primary technique used for pattern recognition. To summarize, PCA finds variables that are linear combinations of original variables. The new variables are orthogonal to each other. The PCA can be used to find clusters in a set of data. Once clusters are found they can then be used for pattern classification. The patterns can then be mapped to mental states, as described below.

It has been shown that the relaxed solution of K-means clustering, specified by the cluster indicators, is given by the PCA principal components, and the RCA subspace spanned by the principal directions is identical to the cluster centroid-subspace specified by the between-class scatter matrix. Thus, PCA automatically projects to the subspace where the global solution of K-means clustering lies, and thus facilitates K-means clustering to find near-optimal solutions. Further, a combination of K-means clustering and/or RCA can be efficiently used to complete the delineation of the data into independent clusters.

IV. Data Analysis Tools 4: Pattern Classification Analysis

After the clusters are formed, pattern classification can be performed upon the data. The following procedure is one example of the process:

Pattern classification is the organization of patterns into groups, with each group sharing the same properties, such as a given emotional state, (joy vs. anger). We then define a set of schema to be used for classification. These schemas should be independent of each other. Once we chose a set of schema, they can be used to classify into patterns. The classified patterns can then be used to extract the emotional state for the subject.

One potential problem is that there may not be crisp separation/boundaries between patterns. This occurs where other nonlinear classifiers, such as state vector machines, have been advocated with good results at the expense of computational loads. There are algorithms for such nonlinear classifiers that can be utilized as needed.

V. Data Analysis Tools 5: Support Vector Machine (SVM)

Starting with the data, the support vector machine algorithms attempt to construct a set of hyper-planes, which can be used for classification, regression or other tasks. Whereas the original problem concerns data is in a finite dimensional space, the sets to discriminate and classify may not be linearly separable into that space. The main concept behind the SVM algorithm is to map the original finite dimensional space into a higher dimensional space in which the discrimination and classification can be performed much easier. The vectors defining the hyper planes can be chosen to be linear combinations of feature vectors that occur in the database with some parameters $\alpha i$. With this definition of the hyper plane the points x in the feature space that are mapped into the hyper plane are defined by:

The choice of a suitable kernel function, K, then defines the hyper plane. A number of choices have been proposed and investigated in the literature depending on linear or nonlinear classification schemes.

To illustrate, consider a set of feature vectors $\{xi\}$ where each xi is a p-dimensional, real vector. Any hyper plane can be written as the set of points x satisfying w·x−b=0, where w is the vector normal to the hyper plane and wx is the scalar product of the vectors w and x. The parameter (b.parallel.w.parallel.) determines the offset of the hyper plane from the origin along the normal vector w. If the data are linearly separable, the idea is to select hyper planes in such a way that there are no data points between them, and we try to maximize the distance between them. This is an example of a linear SVM. The original SVM concept was invented by Vladimir N. Vapnik and a number of variants have been proposed by various investigators since then. Depending on choice of the Kernel function, K, a number of nonlinear classification algorithms have also been investigated and implemented in the literature.

There have also been a number of recent investigations attempting to map the feature data onto distinct nonlinear manifolds. The idea is that in terms of manifolds, the pattern recognition and classification becomes more efficient. Our analytics implement the manifold-concept-based algorithms, when the linear classifications are unsuccessful in certain instances. In practice, for the data analysis proposed here, we start with the simplest of the algorithms first and, depending on the needs, use other more complex algorithms. The ultimate goal of these tools is to classify the multi-dimensional feature data into patterns that can be mapped to mental stares.

VI. Data Analysis Tools 6: Risk Assessment and Classification

Once inference has been made about the mental/physiological state of the individual, the severity of the state has to be assessed and the individual grouped/classified into a low, medium, or high-risk category. Empirical methods, Bayesian-based or fuzzy-logic-based methods can be employed for a reliable risk classification.

VII. Data Analysis Tools 7: Visualization of Raw Data and Analysis Tools

Visualization tools will be assembled for one, two, and three-dimensional plots of data as needed. A graphical user interface will be designed for the processing toolbox to process raw data in a plug and play fashion. The algorithms implementing these tools will be developed in C language so that they can be easily ported to DSP chips on a board that can be inserted into a workstation hardware.

VIII. Multiple Stimuli

The analysis presented in this section so far corresponds to a single stimulus. it is straightforward to extend this to multiple stimuli. The volume of data increases by several orders of magnitude depending on the number of stimuli.

The invention claimed is:

1. A system for capturing and processing clinical observations of responses and reactions of an individual to record in real time in different settings to enable a clinician to diagnose, devise a treatment plan for, and/or monitor a mental state of the individual, the system comprising:
one or more computer processors; and
memory comprising machine executable instructions that, upon execution by the one or more computer processors, cause the one or more computer processors to perform a method comprising:
acquiring, using sensors controlled by at least one processor of a system of hardware, a baseline of objective data that quantify biometric and physiological parameters and speech content and verbal communication responses of the individual to stimuli, the sensors comprising biometric sensors, thermal infrared video cameras, and audio-visual cameras that simultaneously capture the biometric and physiological parameters and the speech content and verbal communication responses of the individual as analog signals, digital signals, video data, raw or processed image files, and/or linguistic text captured from oral responses of the individual, the audio-visual and thermal infrared video cameras simultaneously capturing at least one of facial features, pupil size changes, eyelid flutter rates, perspiration, and facial blood flow changes in the visible and infrared spectrums, the audio-visual cameras simultaneously recording the speech content and verbal communication responses of the individual, the speech content and verbal communication responses comprising tone fluctuations, tone perturbations, speech rate, speech patterns, and linguistic content of the individual in response to the stimuli;
obtaining, using the sensors controlled by the at least one processor of the system of hardware, an initial set of the objective data that quantify an initial set of the biometric and physiological parameters and recording, using the audio-visual cameras, an initial set of the speech content and verbal communication responses of the individual to the stimuli selected and administered in a clinical environment by a clinician during a mental state examination of the individual, wherein the stimuli are presented through visual, oral, aural, kinesthetic, and/or written methods;

generating and visualizing, using the at least one processor of the system of hardware, the initial set of the objective data;

repeating the obtaining step to obtain, using the sensors controlled by the at least one processor of the system of hardware, subsequent successive sets of the objective data that quantify subsequent successive sets of the biometric and physiological parameters and to record, using the audio-visual cameras, subsequent successive sets of the speech content and verbal communication responses of the individual to the stimuli selected and administered in a clinical environment by a clinician during subsequent successive sets of mental state examinations of the individual;

repeating the generating and visualizing step, using the at least one processor of the system of hardware, to generate and visualize the subsequent successive sets of the objective data;

transferring, using the at least one processor of the system of hardware, the baseline, initial and subsequent successive sets of the objective data to a database to produce an individual record containing the baseline, initial and subsequent successive sets of the objective data;

quantitatively comparing, using the at least one processor of the system of hardware, the baseline of the objective data and the initial and subsequent successive sets of the objective data contained in the individual record to detect changes in the biometric and physiological parameters and quantitatively comparing, using the at least one processor of the system of hardware, recordings of the speech content and verbal communication responses of the individual to detect changes in the tone fluctuations, the tone perturbations, the speech rate, the speech patterns, and the linguistic content of the individual corresponding to changes in at least one mental health condition of the individual;

processing, using the at least one processor of the system of hardware, the objective data and the initial and subsequent successive sets of objective data to classify the biometric and physiological parameters and the speech content and verbal communication responses of the individual as multidimensional feature data, use data analytics, mathematical tools, and machine learning algorithms in real time to extract and divide the multidimensional feature data into clusters, and perform pattern classification on the clusters to extract the mental state of the individual;

creating, using the at least one processor of the system of hardware, a risk classification and a visualization of the multidimensional feature data, the pattern classification, and the clusters based upon severity of the mental state of the individual; and generating patient illness condition and information of the individual by integrating the changes in the biometric and physiological parameters and the speech content and verbal communication responses of the individual and inferences drawn by a clinician from the mental state examinations of the individual, diagnosed illnesses and conditions information of the individual, medical histories of the individual, and changes in the medical histories of the individual.

2. The system of claim 1, wherein the stimuli are selected from a database of questions, mental and physical activities, or psychometric and aptitude tests.

3. The system of claim 1, wherein the biometric and physiological parameters are selected from the group consisting of: blood pressure, pulse rate, respiratory rate, breathing rate, blood oxygenation level, galvanic skin conductance, facial skin tone, changes in pupil size, tracking pupil movements, changes and frequency of eyelid flutter, changes in sitting postures or bodily movements, gestures or motions, movement of the leg or hand muscles, changes in facial muscles, brain electrical activity, and heart electrical activity.

4. The system of claim 1, wherein the system further includes event monitoring device systems that capture objective measurements of a dynamic stress event and develop a comprehensive patient illness condition.

5. The system of claim 1, wherein the system further includes means for patient feedback and visualization of objective comparisons of illness progress between successive visits.

6. The system of claim 4, wherein the objective measurements include longitudinal information.

7. The system of claim 1, wherein the method performed by the one or more computer processors provides language and verbal response analytics that indicate significant changes, if any, of the coping mechanisms of the individual to manage pressures, stresses and self-control.

8. The system of claim 1, wherein the method performed by the one or more computer processors further comprises assessing resilience of the individual based on the quantitative comparing of the first and subsequent objective records.

9. The system of claim 1, wherein the method performed by the one or more computer processors further comprises assessing coping skills of the individual based on the quantitative comparing of the first and subsequent objective records.

10. The system of claim 1, wherein the method performed by the one or more computer processors further comprises assessing dysfunctionality of the individual based on the quantitative comparing of the first and subsequent objective records.

11. The system of claim 1, wherein the method performed by the one or more computer processors further comprises assessing treatment efficacy of the individual based on the quantitative comparing of the initial and subsequent objective records.

12. The system of claim 1, wherein the method performed by the one or more computer processors further comprises a progression in response to prescribed treatment plans.

13. The system of claim 1, wherein the method performed by the one or more computer processors further comprises the integration of results of toxicity, laboratory, pharmacogenetic, and radiology imaging interpretations and data of the individual as further medical information to the clinician.

14. The system of claim 1, wherein the method performed by the one or more computer processors further comprises the linking and integrating additional information from mental health, physical health, sleep records, or addiction history of the individual to infer changes in the mental state of the individual.

15. The system of claim 1, wherein the system of hardware further comprises:
a biometric data recording system in a clinical office, a mobile real time episode or event data recording device system, or a wearable device recording system.

16. The system of claim 15, wherein the system of hardware further comprises one or more of the sensors that are integrated into one or more devices for gathering real time somatic and autonomic nervous system responses and reactions from the individual in the different clinical and individual settings.

17. The system of claim 16, wherein the one or more devices are located in a clinical setting for use in a clinical examination, or comprise a portable device, or comprise a wearable device for wearing by the individual when the individual is experiencing an anxiety episode or panic attack.

18. The system of claim 15, wherein the system of hardware comprises the sensors that are integrated into one or more devices with user option to select one or more of the sensors, and into one or more devices that process, analyze and fuse raw output data of the one or more sensors through software programs and analytical tools.

19. The system of claim 18, further comprising means for transmitting raw output data of the sensors to a cloud-based server architecture for processing, analysis and integration into an information database.

20. The system of claim 19, wherein the information database is connected to remote testing locations and stores all of the raw output data, analytical tools and software programs.

21. The system of claim 20, wherein the information database performs real time analyses and computations, graphics-based applications and data storage.

22. The system of claim 20, wherein the information database contains medical records of the individual.

23. The system of claim 15, wherein the system of hardware comprises the biometric data recording system, the biometric data recording system comprising integrated multi sensor systems employing image, audio, and digital and analog sensor data fusion techniques and tools.

24. The system of claim 23, wherein the image tools include pairs of the thermal infrared video cameras and the audio-visual cameras to capture the facial features, pupil size changes, eyelid flutter rates, perspiration, and facial blood flow changes of the individual.

25. The system of claim 24, wherein the data recording systems that record speech with different levels of sensitivity, precision and specifications.

26. The system of claim 24, wherein the data recording systems comprise one or more of the sensors capture and measure changes in the biometric and physiological parameters selected from: blood pressure, pulse rate, respiratory rate, breathing rate, blood oxygenation level, galvanic skin conductance, facial skin tone, changes in pupil size, tracking pupil movements, changes and frequency of eyelid flutter, changes in sitting postures or bodily movements, unusual gestures or motions, movement of the leg or hand muscles, changes in voice pitch and tone and perturbation and speech rate, changes in facial muscles, brain electrical activity, and heart electrical activity.

27. The system of claim 26, wherein the one or more of the sensors are connected to the system of hardware with Bluetooth and/or WiFi communication capability.

28. The system of claim 15, wherein the system of hardware comprises the mobile real time episode or event data recording device system or the wearable device recording system, the system of hardware monitors different illnesses for a plurality of individuals in their daily activities and optionally activates customized pre-recorded therapy sessions for the different illnesses for the plurality of individuals.

29. The system of claim 28, the system of hardware further comprising multi sensor integrated devices with data fusion analytics designed to monitor and record vital parameters, sleep patterns and self-reported changes of the plurality of individuals in their daily life patterns over a specific time period.

30. The system of claim 15, wherein the different clinical and individual settings and situations are selected from the group consisting of: periodic or emergency clinical physical and mental health examinations, psychometric testing and measurement sessions, recording and monitoring physiological parameters in daily activities, and during an episode of anxiety, stress, or panic attack.

31. The system of claim 15, wherein the audio-visual cameras comprise at least two integrated audio-visual cameras to record speech and tone, verbal response linguistic content, facial features and pupil size and changes.

32. The system of claim 15, wherein the system of hardware communicates by Bluetooth or Wifi.

33. The system of claim 15, wherein the system of hardware sends medical records of the individual to decision makers in real time.

* * * * *